(12) United States Patent
Kurose

(10) Patent No.: US 9,315,871 B2
(45) Date of Patent: Apr. 19, 2016

(54) MUTATION DETECTION PROBE, MUTATION DETECTION METHOD, METHOD OF EVALUATING DRUG EFFICACY, AND MUTATION DETECTION KIT

(71) Applicant: ARKRAY, Inc., Kyoto (JP)

(72) Inventor: Kaoru Kurose, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 176 days.

(21) Appl. No.: 14/029,831

(22) Filed: Sep. 18, 2013

(65) Prior Publication Data

US 2014/0087380 A1 Mar. 27, 2014

(30) Foreign Application Priority Data

Sep. 24, 2012 (JP) ................................ 2012-210057
Sep. 9, 2013 (JP) ................................ 2013-186532

(51) Int. Cl.
*C12Q 1/68* (2006.01)

(52) U.S. Cl.
CPC ............ *C12Q 1/6886* (2013.01); *C12Q 1/6827* (2013.01); *C12Q 2600/156* (2013.01)

(58) Field of Classification Search
CPC ........... C12Q 1/6827; C12Q 2527/107; C12Q 2537/143
See application file for complete search history.

(56) References Cited

U.S. PATENT DOCUMENTS

2010/0216123 A1* 8/2010 Hirai et al. ........................ 435/6
2011/0256546 A1 10/2011 Morris et al.

FOREIGN PATENT DOCUMENTS

JP 2002-119291 A 4/2002
WO 2011/095894 A2 8/2011

OTHER PUBLICATIONS

GenBank GU: 128154, *Homo sapiens* L1196M mutant anaplastic lymphoma receptor tyrosine kinase (ALK) mRNA, complete cds. (Nov. 17, 2009), from www.ncbi.nlm.nih.gov, pp. 1-3.*
Extended European Search Report issued in corresponding European Patent Application No. 13185833.4 dated Dec. 9, 2013.
Choi et al., "EML4-ALK Mutations in Lung Cancer that Confer Resistance to ALK Inhibitors," New England Journal of Medicine, 363: 1734-1739 (2010).

* cited by examiner

*Primary Examiner* — Stephen Kapushoc
(74) *Attorney, Agent, or Firm* — Morgan, Lewis & Bockius LLP

(57) ABSTRACT

The present invention provides a probe for detecting a mutation in the ALK gene, which is at least one fluorescently labeled oligonucleotide selected from the group consisting of P1 to P4, P7 and P8 oligonucleotides; an application thereof; and an oligonucleotide for the application.

11 Claims, 8 Drawing Sheets

MUTATION DETECTION PROBE, MUTATION DETECTION METHOD, METHOD OF EVALUATING DRUG EFFICACY, AND MUTATION DETECTION KIT

SEQUENCE LISTING SUBMISSION VIA EFS-WEB

A computer readable text file, entitled "SequenceListing.txt" created on or about Sep. 16, 2013, with a file size of about 11 kb contains the sequence listing for this application and is hereby incorporated by reference in its entirety.

BACKGROUND

1. Technical Field

The present invention relates to a probe for detecting a mutation, a method of detecting a mutation, a method of evaluating the efficacy of a drug, and a kit for detecting a mutation.

2. Related Art

One of the causes for the onset of lung cancer is a gene mutation. Therefore, there is an ongoing effort to identify a gene that is thought to be associated with the onset of lung cancer. Examples of such a gene mutation that is believed to be associated with the onset of lung cancer include an EGFR gene mutation and an ALK gene mutation.

The ALK (Anaplastic Lymphoma Kinase) gene encodes a receptor tyrosine kinase and is known to be fused with the EML4 gene when an inversion occurs in the second chromosome. It is believed that a constitutively activated tyrosine kinase is produced by the work of this fusion gene (EML4-ALK), inducing the onset of lung adenocarcinoma. Thus, the use of an ALK inhibitor has been tried in the field of lung cancer treatment. As such an ALK inhibitor, crizotinib is known.

However, although crizotinib has been observed to have a certain therapeutic effect in early stages, the effect of this agent may be gradually reduced more than expected.

It has been discovered that the expression of such an inhibitory activity is associated with two mutations occurring in the EML4-ALK gene, namely a mutation in which the 1156th cytosine in the amino acid sequence of the ALK gene is substituted with tyrosine (hereinafter, sometimes referred to as "ALK(C1156Y)") and a mutation in which the 1196th leucine in the amino acid sequence of the ALK gene is substituted with methionine (hereinafter, sometimes referred to as "ALK(L1196M)") (see the New England Journal of Medicine, Vol. 363, pp. 1734-1739, (2010)). It has been proven that these gene mutations show a common property in that they occur at the crizotinib-binding pocket site in the EML4-ELK fusion gene and consequently alter the shape of the binding pocket to reduce the binding affinity between crizotinib and the EML4-ALK fusion gene. Accordingly, in the use of an ALK inhibitor, it is important to detect the presence or absence of these ALK gene mutations as a factor for predicting the effect of the ALK inhibitor.

Meanwhile, in recent years, melting curve analysis (Tm analysis) has been utilized for a test for detecting a gene mutation. In this method, after amplifying a mutation-containing region by a PCR method, a melting curve analysis is performed using a nucleic acid probe labeled with a fluorescent dye so as to analyze a mutation in a base sequence based on the results of the melting curve analysis (see, for example, Japanese Patent Application Laid-Open (JP-A) No. 2002-119291).

SUMMARY OF THE INVENTION

In the New England Journal of Medicine, Vol. 363, pp. 1734-1739 (2010), the gene mutations are each directly detected based on the respective sequences by a so-called direct sequencing method; however, this method is laborious and costly in that, for example, after performing DNA extraction and purification as well as PCR, a sequencing reaction and electrophoresis by a sequencer must be carried out. In addition, the resulting amplification product may contaminate other reactions. Furthermore, automation of this method is difficult and plural nucleic acid sequences cannot be examined simultaneously.

JP-A No. 2002-119291 discloses a method in which a nucleic acid probe labeled with a fluorescent dye is hybridized to a target nucleic acid and the reduction in the amount of luminescence by the fluorescent dye is measured. However, these steps of hybridizing a nucleic acid probe labeled with a fluorescent dye to a target nucleic acid and measuring the reduction in the luminescence by the fluorescent dye are not necessarily applicable to all arbitrary sequences; therefore, an appropriate sequence must be found for each mutation.

In view of these present circumstances, for example, for the purpose of predicting the effect of an ALK inhibitor, a further development of a technology effective for detecting a mutation in the ALK(L1196M) mutant-type and ALK(C1156Y) mutant-type ALK genes has been strongly desired.

An object of the present invention is to provide a mutation detection probe which allows easy detection of a mutation in the ALK gene; a method of detecting a mutation that utilizes the mutation detection probe; a method of evaluating the efficacy of a drug that utilizes the mutation detection probe; and a mutation detection kit.

Embodiments of the present invention provide the following mutation detection probes for detecting a mutation in the ALK gene; methods of detecting a mutation; methods of evaluating the efficacy of a drug; reagent kits for detecting a mutation; and fluorescently labeled oligonucleotides.

[1] A mutation detection probe for detecting a mutation in the ALK gene, the mutation detection probe including at least one fluorescently labeled oligonucleotide selected from the group consisting of the following oligonucleotides:

(P1) an oligonucleotide having the base sequence indicated in SEQ ID NO:5, wherein cytosine at the 3'-end is labeled with a fluorescent dye;

(P2) an oligonucleotide having the base sequence indicated in SEQ ID NO:6, wherein cytosine at the 3'-end is labeled with a fluorescent dye;

(P3) an oligonucleotide having the base sequence indicated in SEQ ID NO:7, wherein cytosine at the 5'-end is labeled with a fluorescent dye;

(P4) an oligonucleotide having the base sequence indicated in SEQ ID NO:8, wherein cytosine at the 3'-end is labeled with a fluorescent dye;

(P7) an oligonucleotide having the base sequence indicated in SEQ ID NO:9, wherein cytosine at the 5'-end is labeled with a fluorescent dye; and (P8) an oligonucleotide having the base sequence indicated in SEQ ID NO:10, wherein cytosine at the 3'-end is labeled with a fluorescent dye.

[2] The mutation detection probe according to [1], wherein the fluorescently labeled oligonucleotide emits fluorescence when not hybridized to a target sequence, and a fluorescence intensity of the fluorescently labeled oligonucleotide when hybridized to the target sequence is decreased or increased as compared to when not hybridized to the target sequence.

[3] The mutation detection probe according to [2], wherein the fluorescently labeled oligonucleotide emits fluorescence when not hybridized to a target sequence, and the fluorescence intensity of the fluorescently labeled oligonucleotide when hybridized to the target sequence is decreased as compared to when not hybridized to the target sequence.

[4] The mutation detection probe according to any one of [1] to [3], which is a probe for melting curve analysis.

[5] A method of detecting a mutation in the ALK gene, the method including:
detecting at least one of a mutation at the 133rd base of the base sequence indicated in SEQ ID NO:1 or a mutation at the 244th base of the base sequence indicated in SEQ ID NO:3 by using the mutation detection probe according to any one of [1] to [4].

[6] The method according to [5], wherein at least one of the mutation at the 133rd base of the base sequence indicated in SEQ ID NO:1 or the mutation at the 244th base of the base sequence indicated in SEQ ID NO:3 is detected in the same system.

[7] The method according to [5] or [6], the method including the processes of:
(I) bringing the mutation detection probe according to any one of [1] to [4] into contact with a single stranded nucleic acid contained in a sample to hybridize the fluorescently labeled oligonucleotide to the single-stranded nucleic acid, to obtain a hybrid;
(II) dissociating the hybrid by changing a temperature of the sample containing the hybrid so as to measure the change in a fluorescence signal caused by dissociation of the hybrid;
(III) determining a Tm value, which is a dissociation temperature of the hybrid, based on the change in the fluorescence signal; and
(IV) detecting the presence of a mutation in the ALK gene in the single-stranded nucleic acid contained in the sample, based on the Tm value.

[8] The method according to [7], further including:
amplifying the nucleic acid prior to or simultaneously with the process (I) of obtaining a hybrid.

[9] The method according to [7], further including:
detecting a mutation at the 133rd base of the base sequence indicated in SEQ ID NO:1 by using the mutation detection probe according to any one of [1] to [4]; and
amplifying the nucleic acid using the following P5 and P6 primers:
(P5) a primer having the base sequence indicated in SEQ ID NO:14; and
(P6) a primer having the base sequence indicated in SEQ ID NO:15.

[10] A method of evaluating efficacy of a drug, the method including:
detecting a mutation in the ALK gene by the method of detecting a mutation according to any one of [5] to [9]; and
determining tolerance to a drug or efficacy of the drug based on the presence or absence of a detected mutation.

[11] A reagent kit for detecting a mutation in the ALK gene, the reagent kit including the mutation detection probe according to any one of [1] to [4].

[12] The reagent kit according to [11], further including at least one of the following primers:
a primer for amplifying a base sequence containing a region to which the P1, P2, P3, P7 or P8 oligonucleotide hybridizes; or
a primer for amplifying a base sequence containing a region to which the P4 oligonucleotide hybridizes.

[13] A fluorescently labeled oligonucleotide, which is any one of the following oligonucleotides:
an oligonucleotide having the base sequence indicated in SEQ ID NO:5, wherein cytosine at the 3'-end is labeled with a fluorescent dye;
an oligonucleotide having the base sequence indicated in SEQ ID NO:6, wherein cytosine at the 3'-end is labeled with a fluorescent dye;
an oligonucleotide having the base sequence indicated in SEQ ID NO:7, wherein cytosine at the 5'-end is labeled with a fluorescent dye;
an oligonucleotide having the base sequence indicated in SEQ ID NO:8, wherein cytosine at the 3'-end is labeled with a fluorescent dye;
an oligonucleotide having the base sequence indicated in SEQ ID NO:9, wherein cytosine at the 5'-end is labeled with a fluorescent dye; or
an oligonucleotide having the base sequence indicated in SEQ ID NO:10, wherein cytosine at the 3'-end is labeled with a fluorescent dye.

DETAILED DESCRIPTION OF THE INVENTION

Figure 1A:
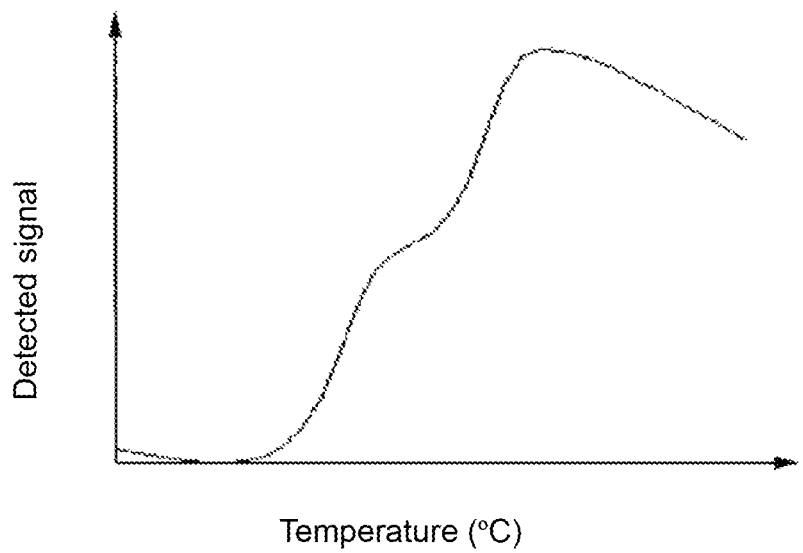
FIG. 1A shows an example of a melting curve of a nucleic acid mixture.

The probe for detecting a mutation in the ALK gene according to the present invention (hereinafter, may be simply referred to as "the mutation detection probe") is a mutation detection probe including at least one fluorescently labeled oligonucleotide selected from the group consisting of the above-described P1, P2, P3, P4, P7 and P8 fluorescently labeled oligonucleotides.

The method of detecting a mutation in the ALK gene according to the present invention is a method which includes detecting at least one of a mutation at the 133rd base of the base sequence indicated in SEQ ID NO:1 or a mutation at the 244th base of the base sequence indicated in SEQ ID NO:3 by using the mutation detection probe of the present invention.

The method of evaluating the efficacy of a drug according to the present invention is a method which includes the processes of: detecting a mutation in the ALK gene by the method of detecting a mutation in the ALK gene of the present invention; and determining the tolerance to the drug or the efficacy of the drug based on the detected presence or absence of detected mutation.

Further, the reagent kit for detecting a mutation according to the present invention is a reagent kit for detecting a mutation in the ALK gene, the reagent kit including the mutation detection probe of the present invention.

Specifically, in the present invention, by designing a fluorescently labeled oligonucleotide which contains a base corresponding to a base showing mutation and has a fluorescently labeled cytosine at a specific position, a mutation detection probe which is applicable to a detection method capable of automatically detecting a mutation, such as melting curve analysis, can be obtained and a target ALK gene mutation can be easily detected. Further, by using the mutation detection probe, the efficacy of a drug can be simply evaluated based on the ALK gene mutation.

The "ALK gene" in the present invention is already known, and the base sequence thereof corresponds to the 29415640th to the 30144477th bases of NCBI Reference Sequence: NC 000002.11. In the present specification, unless otherwise specified, the "ALK gene" means the base sequence indicated in SEQ ID NO:2 or SEQ ID NO:4.

The base sequence of SEQ ID NO:1 is a mutant-type base sequence in which the 1st to the 300th bases thereof correspond to the 8265650th to the 8265351st bases of NCBI Reference Sequence: NT_022184.15 and the 133rd base corresponding to the 8265518th base is "A (adenine)".

The base sequence of SEQ ID NO:2 is a wild-type base sequence in which the 1st to the 300th bases correspond to the 8265650th to the 8265351st bases of NCBI Reference Sequence: NT_022184.15 and the 133rd base corresponding to the 8265518th base is "C (cytosine)".

The base sequence of SEQ ID NO:3 is a mutant-type base sequence in which the 1st to the 300th bases correspond to the 8267388th to the 8267089th bases of NCBI Reference Sequence: NT_022184.15 and the 244th base corresponding to the 8267145th base is "A (adenine)".

The base sequence of SEQ ID NO:4 is a wild-type base sequence in which the 1st to the 300th bases correspond to the 8267388th to the 8267089th bases of NCBI Reference Sequence: NT_022184.15 and the 244th base corresponding to the 8267145th base is "G (guanine)".

In the present invention, the descriptions of the base sequences of the sample nucleic acid in a sample to be detected and the polymorphism detection probe or primer shall also apply to complementary base sequences thereof, respectively, unless otherwise specified. Further, when the description of a particular base sequence is applied to a complementary base sequence thereof, descriptions of base sequences recognized by the particular base sequence in the present invention should be applied provided that the recognition by the particular base sequence should be replaced with recognition by a complementary base sequence of the particular base sequence, within a range of the common general technical knowledge of those skilled in the art.

In the present invention, the term "Tm value" is defined as a temperature at which a double-stranded nucleic acid dissociates (dissociation temperature: Tm), and is generally defined as a temperature at which the absorbance at 260 nm has increased by 50% of the total increase in absorbance resulting from complete dissociation of the double-stranded nucleic acid. More specifically, when a solution containing a double-stranded nucleic acid such as a double-stranded DNA is heated, the absorbance at 260 nm of the double-stranded nucleic acid gradually increases. This is because the hydrogen bonds between both strands of the double-stranded DNA are broken by heating, thereby dissociating the double-stranded DNA into single-stranded DNAs (melting of DNA). When the double-stranded DNA has completely dissociated into single-stranded DNAs, the single-stranded DNAs exhibit an absorbance that is about 1.5 times the absorbance at the time of the initiation of the heating (i.e., the absorbance when the entire DNA is in the form of a double-stranded DNA), which serves as an indicator of the completion of the melting. The Tm value is defined based on this phenomenon. The "Tm value" in the present invention means the temperature at which the absorbance at 260 mm has increased by 50% of the total increase in absorbance, unless specifically defined.

In the present invention, in cases in which a Tm value is calculated, the Tm value is calculated using a software "Meltcalc 99 free" (http://www.meltcalc.com/) under the following conditions: Oligoconc [μM]=0.2, Na eq. [mM]=50, unless otherwise specified. This software is known in the art and used for designing a probe also in Clinical Chemistry Vol. 54, No. 6, pp. 990-999 (2008) and the like.

In the present invention, when the phrase "the first to third bases from the 3' end" is used in connection to an oligonucleotide sequence, it is assumed that the base at the 3' end of the oligonucleotide chain is the first base from the 3' end. Similarly, when the phrase "the first to third bases from the 5' end" is used in connection to an oligonucleotide sequence, it is assumed that the base at the 5' end of the oligonucleotide chain is the first base from the 5' end.

In the present invention, the "oligonucleotide" in the fluorescently labeled oligonucleotide mentioned above encompasses oligonucleotides as well as modified oligonucleotides.

Examples of a structural unit of the oligonucleotide include ribonucleotides, deoxyribonucleotides and artificial nucleic acids. Examples of the artificial nucleic acids include DNAs, RNAs, LNAs (Locked Nucleic Acids) which are RNA analogues, PNAs (Peptide Nucleic Acids) which are peptide nucleic acids, and BNAs (Bridged Nucleic Acids) which are cross-linked nucleic acids.

The oligonucleotides may each be constituted from one type or plural types of the above-mentioned structural units.

The hybridization may be carried out according to a known method or a method corresponding thereto, such as a method as described in Molecular Cloning 3rd (J. Sambrook et al., Cold Spring Harbor Lab. Press, 2001). This document is incorporated herein by reference.

In the present specification, the scope of the term "process" includes not only a discrete process, but also a process that cannot be clearly distinguished from another process as long as the expected effect of the process of interest is achieved.

In the present specification, any numerical range expressed using "to" refers to a range including the numerical values before and after "to" as the minimum and maximum values, respectively.

In a case in which the amount of a component that may be included in the composition is indicated in the present invention, when there are plural substances corresponding to the component in the composition, the indicated amount means the total amount of the plural substances present in the composition, unless specifically stated otherwise.

In the present specification, the term "mutation" refers to a base sequence newly produced by substitution, deletion, overlapping or insertion of a part of a wild-type base sequence.

Hereinbelow, the present invention is described.

<Probe for Detecting Mutation in ALK Gene>

The probe for detecting a mutation in the ALK gene according to the present invention (hereinafter, may be simply referred to as "mutation detection probe") is a probe for detecting a mutation in the ALK gene, which is at least one fluorescently labeled oligonucleotide selected from the group consisting of the fluorescently labeled oligonucleotides P1, P2, P3, P4, P7 and P8 mentioned above.

In the wild-type ALK gene, the base corresponding to the 133rd base of the sequence indicated in SEQ ID NO:1 is C (cytosine). Meanwhile, in a mutant-type, the cytosine in the wild-type is mutated to A (adenine) (hereinafter, also referred to as "ALK(L1196M) mutant-type") and this base corresponds to the 8265518th base in the 8265650th to the 8265351st bases of the ALK gene.

In the wild-type ALK gene, the base corresponding to the 244th base of the sequence indicated in SEQ ID NO:3 is G (guanine). Meanwhile, in a mutant-type, the guanine in the wild-type is mutated to A (adenine) (hereinafter, also referred to as "ALK(C1156Y) mutant-type") and this base corresponds to the 8267145th base in the 8267388th to the 8267089th bases of the ALK gene.

The P1, P2, P3, P7 and P8 fluorescently labeled oligonucleotides are probes capable of detecting the ALK(L1196M) mutation and the P4 fluorescently labeled oligonucleotide is a probe capable of detecting the ALK(C1156Y) mutation. It is possible to detect a mutation in the ALK gene by using the mutation detection probes that are fluorescently labeled oligonucleotides.

The base sequences of the P1, P2, P3, P4, P7 and P8 fluorescently labeled oligonucleotides are shown in Table 1.

The P1 fluorescently labeled oligonucleotide has a base sequence complementary to a 17-base-long sequence composed of the 123rd to the 139th bases of the base sequence indicated in SEQ ID NO:1, in which the base corresponding to the 123rd base is cytosine. In the P1 fluorescently labeled oligonucleotide, the cytosine at the 3'-end of the P1 oligonucleotide, which corresponds to the 123rd base of the base sequence indicated in SEQ ID NO:1, is labeled with a fluorescent dye.

The P2 fluorescently labeled oligonucleotide has a 19-base-long sequence composed of the 123rd to the 141st bases of the base sequence indicated in SEQ ID NO:1, in which the base corresponding to the 141st base is cytosine. In the P2 fluorescently labeled oligonucleotide, the cytosine at the 3'-end of the P2 oligonucleotide, which corresponds to the 141st base of the base sequence indicated in SEQ ID NO:1, is labeled with a fluorescent dye.

The P3 fluorescently labeled oligonucleotide has a base sequence complementary to a 16-base-long sequence composed of the 123rd to the 138th bases of the base sequence indicated in SEQ ID NO:2, in which the base corresponding to the 138th base is cytosine. In the P3 fluorescently labeled oligonucleotide, the cytosine at the 5'-end of the P3 oligonucleotide, which corresponds to the 138th base of the base sequence indicated in SEQ ID NO:2, is labeled with a fluorescent dye.

The P4 fluorescently labeled oligonucleotide has an 18-base-long sequence composed of the 235th to the 252nd bases of the base sequence indicated in SEQ ID NO:3, in which the base corresponding to the 252nd base is cytosine. In the P4 fluorescently labeled oligonucleotide, the cytosine at the 3'-end of the P4 oligonucleotide, which corresponds to the 252nd base of the base sequence indicated in SEQ ID NO:3, is labeled with a fluorescent dye.

The P7 fluorescently labeled oligonucleotide has a base sequence complementary to a 17-base-long sequence composed of the 129th to the 145th bases of the base sequence indicated in SEQ ID NO:2, in which the base corresponding to the 129th base is cytosine. In the P7 fluorescently labeled oligonucleotide, the cytosine at the 5'-end of the P7 oligonucleotide, which corresponds to the 129th base of the base sequence indicated in SEQ ID NO:2, is labeled with a fluorescent dye.

The P8 fluorescently labeled oligonucleotide has an 18-base-long sequence composed of the 129th to the 146th bases of the base sequence indicated in SEQ ID NO:1, in which the base corresponding to the 146th base is cytosine. In the P8 fluorescently labeled oligonucleotide, the cytosine at the 3'-end of the P8 oligonucleotide, which corresponds to the 146th base of the base sequence indicated in SEQ ID NO:1, is labeled with a fluorescent dye.

In Table 1, for the P1, P2, P3, P7 and P8 oligonucleotides, the base corresponding to the 133rd base of SEQ ID NO:1 is indicated with a capital letter. In addition, Table 1 also shows the Tm values that were calculated for the hybrids formed between a sample nucleic acid in which the base corresponding to the 133rd base of SEQ ID NO:1 is C (wild-type) or A (mutant-type) and the respective fluorescently labeled oligonucleotides.

Further, in Table 1, for the P4 oligonucleotide, the base corresponding to the 244th base of SEQ ID NO:3 is indicated with a capital letter. Table 1 also shows the Tm values that were calculated for the hybrids formed between a sample nucleic acid in which the base corresponding to the 244th base of SEQ ID NO:3 is G (wild-type) or A (mutant-type) and the fluorescently labeled oligonucleotide.

TABLE 1

|    |                    | Length (mer) | Tm value WT | Tm value mt | Δ value | SEQ. ID No. |
|----|--------------------|--------------|-------------|-------------|---------|-------------|
| P1 | gctccaTcaggatgaac  | 17           | 39.8        | 48.2        | 8.4     | 5           |
| P2 | gttcatcctgAtggagctc| 19           | 48.1        | 51.3        | 3.3     | 6           |
| P3 | ctccaGcaggatgaac   | 16           | 47.4        | 39.2        | 8.2     | 7           |
| P4 | ctgaagtgtActctgaac | 18           | 37.9        | 45.8        | 7.9     | 8           |

TABLE 1-continued

|  |  | Length (mer) | Tm value WT | Tm value mt | Δ value | SEQ. ID No. |
|---|---|---|---|---|---|---|
| P7 | ccatgagctccaTcagg | 17 | 41 | 46 | 4.6 | 9 |
| P8 | cctgCtggagctcatggc | 18 | 56.9 | 46.6 | 10.3 | 10 |

Δ value: Difference in Tm values (the same applies hereinbelow.)

It is noted that, among the fluorescently labeled oligonucleotides having base sequences in which 1 to 3 bases of the base sequences of the P1, P2, P3, P4, P7 and P8 fluorescently labeled oligonucleotides in the mutation detection probe of the present invention are elongated, shortened, inserted, deleted or substituted, respectively, probes capable of detecting the ALK(L1196M) mutation or the ALK(C1156Y) mutation in the same manner as the mutation detection probe according to the present invention may exist. Among such probes that are fluorescently labeled oligonucleotides having the same base sequence as the mutation detection probe of the present invention except that 1 to 3 bases are elongated, shortened, inserted, deleted or substituted, those capable of detecting a mutation are also encompassed in the present invention.

Among such probes that are fluorescently labeled oligonucleotides having the same base sequences as the P1, P2, P3, P7 or P8 fluorescently labeled oligonucleotide of the mutation detection probes according to the present invention except that 1 to 3 bases thereof are elongated, shortened, inserted, deleted or substituted, which probes recognize a mutation at the 133rd base of SEQ ID NO:1, those capable of detecting a mutation are also encompassed in the present invention.

Here, an expression such as "recognize a mutation at the 133rd base of SEQ ID NO:1" means that the probe "binds to the base exhibiting mutation at the 133rd position of SEQ ID NO:1".

Among such probes that are fluorescently labeled oligonucleotides having the same base sequences as the P4 fluorescently labeled oligonucleotide of the mutation detection probes according to the present invention except that 1 to 3 bases are elongated, shortened, inserted, deleted or substituted, which probes recognize a mutation at the 244th base of SEQ ID NO:3, those capable of detecting a mutation are also encompassed in the present invention.

Here, such an expression "recognizing a mutation at the 244th base of SEQ ID NO:3" means that the probe "binds to the base exhibiting mutation at the 244th position of SEQ ID NO:3".

The fluorescently labeled oligonucleotide of the present invention may be a fluorescently labeled oligonucleotide in which the fluorescence intensity at the time when the oligonucleotide is hybridized to a target sequence thereof is decreased (quenched) or increased as compared to the fluorescence intensity at the time when the oligonucleotide is not hybridized to the target sequence. In particular, the fluorescently labeled oligonucleotide of the present invention may be a fluorescently labeled oligonucleotide in which the fluorescence intensity at the time when the oligonucleotide is hybridized to a target sequence thereof is decreased as compared to the fluorescence intensity at the time when the oligonucleotide is not hybridized to the target sequence.

A probe that utilizes the "fluorescence quenching phenomenon" as described above is generally referred to as a guanine quenching probe, and it is known as Q PROBE®. Among such probes, an oligonucleotide which has been designed so that its 3' or 5' end is a cytosine (C) and which has been labeled with a fluorescent dye so that the fluorescence emission is reduced when the C at the 3' or 5' end comes close to a guanine (G) is especially preferable.

By using such a probe, the hybridization and dissociation of the probe may be readily checked by the change in signal.

A known detection method other than the detection method using a Q PROBE® may also be applied. Examples of such a detection method include a TAQ-MAN probe method, a hybridization probe method, a molecular beacon method, and a MGB probe method.

The fluorescent dye is not particularly limited, and examples of the fluorescent dye include fluorescein, phosphor, rhodamine and polymethine dye derivatives. Examples of commercially available products of such fluorescent dyes include Pacific Blue, BODIPY FL, FluorePrime, Fluoredite, FAM, Cy3 and CyS, and TAMRA.

The detection conditions of the fluorescently labeled oligonucleotide are not particularly limited, and may be decided, as appropriate, in accordance with the fluorescent dye to be used. For example, Pacific Blue can be detected at a detection wavelength of from 445 nm to 480 nm, TAMRA can be detected at a detection wavelength of from 585 nm to 700 nm, and BODIPY FL can be detected at a detection wavelength of from 520 nm to 555 nm.

By using a probe having such a fluorescent dye, hybridization and dissociation of the probe can be readily confirmed based on a change in fluorescence signal thereof. Attachment of a fluorescent dye to the oligonucleotide may be carried out according to an ordinary method, such as a method described in JP-A No. 2002-119291.

The fluorescently labeled oligonucleotide may have, for example, a phosphate group added to the 3'-end thereof. Addition of a phosphate group to the 3'-end of the fluorescently labeled oligonucleotide sufficiently prevents the probe itself from elongation caused by a gene amplification reaction. As described below, a DNA for which the presence or absence of a mutation is to be detected (target DNA) may be prepared by a gene amplification method such as PCR. When the fluorescently labeled oligonucleotide that has a phosphate group added to its 3' end is used, the amplification reaction can be carried out even in the presence of the oligonucleotide in a reaction solution of the amplification reaction.

Substantially the same effect can also be attained by adding such a labeling substance (fluorescent dye) as described in the above to the 3'-end.

The P1, P2, P3, P7 and P8 fluorescently labeled oligonucleotides may each be used as a probe for detecting a mutation in the ALK gene, particularly the ALK(L1196M) mutation, and the probe for detecting a mutation in the ALK gene may be used as a probe for melting curve analysis.

The P4 fluorescently labeled oligonucleotide may be used as a probe for detecting a mutation in the ALK gene, particularly the ALK(C1156Y) mutation, and the probe for detecting a mutation in the ALK gene may be used as a probe for melting curve analysis.

The P1, P2, P3, P7 and P8 fluorescently labeled oligonucleotides can be prepared in accordance with a method known as an oligonucleotide synthesis method, such as the method described in JP-A No. 2002-119291, except that the base corresponding to the 123rd base of the base sequence of SEQ ID NO:1 in a case of the P1 fluorescently labeled oligonucleotide is cytosine that is labeled with a fluorescent dye; the base corresponding to the 141 base of the base sequence of SEQ ID NO:1 in a case of the P2 fluorescently labeled oligonucleotide is cytosine that is labeled with a fluorescent dye; the base corresponding to the 138th base of the base sequence of SEQ ID NO:2 in a case of the P3 fluorescently labeled oligonucleotide is cytosine that is labeled with a fluorescent dye; the base corresponding to the 145th base of the base sequence of SEQ ID NO:1 in a case of the P7 fluorescently labeled oligonucleotide is cytosine that is labeled with a fluorescent dye; and the base corresponding to the 146th base of the base sequence of SEQ ID NO:2 in a case of the P8 fluorescently labeled oligonucleotide is cytosine that is labeled with a fluorescent dye.

Further, the P4 fluorescently labeled oligonucleotide may also be prepared in accordance with a method known as an oligonucleotide synthesis method, such as the method described in JP-A No. 2002-119291, except that the base corresponding to the 252nd base of the base sequence shown in SEQ ID NO:3 is cytosine that is labeled with a fluorescent dye.

<Primer>

In the method of detecting a mutation in the ALK gene described below, a primer is used for amplifying a sequence having an ALK gene mutation to be detected by a PCR method.

The primer that may be used in the present invention is not particularly restricted as long as the primer enables amplification of a nucleic acid containing the base corresponding to the 133rd base of the base sequence indicated in SEQ ID NO:1 when the ALK gene mutation to be detected is the ALK(L1196M) mutation or a nucleic acid containing the base corresponding to the 244th base of the base sequence indicated in SEQ ID NO:3 when the ALK gene mutation to be detected is the ALK(C1156Y) mutation.

The primer to be applied to the PCR method is not particularly restricted as long as the primer is capable of amplifying a base sequence containing a region to which the mutation detection probe of the present invention hybridizes. Those skilled in the art should be able to appropriately design such a primer on the basis of the base sequences indicated in SEQ ID NO:1 to 4. The length of the primer and the Tm value for a single-stranded nucleic acid to which the primer hybridizes may be set at 12 mer to 40 mer and 40° C. to 70° C., or 16 mer to 30 mer and 55° C. to 60° C., respectively.

The lengths of the primers included in a primer set may be the same as or may be different from one another, and the Tm values of the primers may be substantially the same, or the difference between the Tm values of the primers may be 5° C. or less.

In a case in which the method of detecting a mutation in the ALK gene according to the present invention is used for detecting the ALK(L1196M) mutation, a sample nucleic acid can be amplified by using the P5 and P6 primers as primers.

The P5 primer is capable of efficiently amplifying a nucleic acid by utilizing a nucleic acid having the ALK(L1196M) mutant-type base sequence as a template. The P6 primer is capable of efficiently amplifying a nucleic acid by utilizing a nucleic acid having the wild-type base sequence of the ALK gene as a template. Therefore, by using the P5 and P6 primers in combination with the P1, P2, P3, P7 and P8 fluorescently labeled oligonucleotides, the ALK(L1196M) mutation can be detected with good sensitivity. Particularly, the use of the P5 and P6 primers in combination with the P2 fluorescently labeled oligonucleotide enables the detection of the ALK (L1196M) mutation with superior sensitivity.

In the present invention, a nucleic acid having a base sequence to which a primer is capable of hybridizing in a nucleic acid amplification reaction may be referred to as "template nucleic acid".

It is noted that, among the primers having the base sequences of the P5 and P6 primers for detecting a mutation according to the present invention from which 1 to 3 bases are elongated, shortened, inserted, deleted or substituted, respectively, primers that are, in the same manner as the mutation detection primers according to the present invention, capable of detecting the ALK(L1196M) mutation or the ALK (C1156Y) mutation when used in combination with the mutation detection probe according to the present invention may exist. Among such primes that have the same base sequence as the mutation detection primer according to the present invention except that 1 to 3 bases are elongated, shortened, inserted, deleted or substituted, the primers capable of detecting a mutation when used in combination with the mutation detection probe of the present invention are also included in the primer for detecting a mutation according to the present invention.

The base sequences of the P5 and P6 primers (SEQ ID NOs:14 and 15, respectively) each contain a base corresponding to the 133rd base of the base sequence indicated in SEQ ID NO:1 or 2, respectively. In this way, for example, the amplification efficiency of a nucleic acid having a base sequence of interest can be improved.

The P6 primer contains a base which mismatches with the base sequence indicated in SEQ ID NO:2 (mismatch base). The term "mismatch base" means a base which leads to a combination of bases that are different from G (guanine)-C (cytosine) or a combination of bases that are different from A (adenine)-T(thymine), specifically the combination of G-G, G-A, G-T, A-A, A-C, C-T, C-C or T-T.

Examples of the primers that may be used for amplifying a base sequence containing a region to which the mutation detection probe of the present invention used in the method of detecting a mutation according to the present invention hybridizes are shown below. It is noted here, however, that following examples are provided for illustrative purposes only and that the present invention is not restricted thereto.

The ALK L1196M-mt-F10 mentioned below is the P5 primer which has an additional sequence of 7 bases at the 5'-end thereof and has an "A" corresponding to the 133rd base of SEQ ID NO:1 at the 3'-end thereof. The ALK L1196M-WT-F6 is the P6 primer which has an additional sequence of 6 bases at the 5'-end thereof, has a "C" corresponding to the 133rd base of SEQ ID NO:2 at the 3'-end thereof, and has a mismatch base ("a"), which is different from the base corresponding to the 128th base of SEQ ID NO:2, at the fifth position from the 3'-end thereof.

TABLE 2

| name | sequence (5'→3') | mer | SEQ. ID. No. |
|---|---|---|---|
| ALK C1156Y-F1 | ggactctgtaggctgcagttctc | 23 | 11 |
| ALK C1156Y-R4 | tgatcagggcttccatgaggaaatccag | 28 | 12 |
| ALK L1196M F-1 | cattggggtgagcctgcaatc | 21 | 13 |
| ALK L1196M-mt-F10 | tgcatcaccctgccccggttcatcctgA | 28 | 14 |
| ALK L1196M-WT-F6 | ctacgacctgccccggttcaacctgC | 26 | 15 |
| ALK L1196M R-2 | cttggcacaacaactgcagcaaagac | 26 | 16 |
| ALK L1196M R-3 | ggacggacggaccttggcacaacaactgcagcaaagac | 38 | 17 |

The method of detecting a mutation is not particularly restricted as long as it is a method in which the fluorescently labeled nucleotides are used as probes. As one example of the method of detecting a mutation in which the fluorescently labeled nucleotides are used as probes, a method of detecting a mutation by Tm analysis is described below.

<Method of Detecting Mutation>

The method of detecting a mutation in the ALK gene according to the present invention is a method which includes detecting a mutation in the ALK gene by using at least one of the above-described probes for detecting a mutation in the ALK gene.

According to the mutation detection method of the present invention, by using at least one of the above-described mutation detection probes, a mutation in the ALK gene, particularly at least one of the ALK(L1196M) mutation or the ALK (C1156Y) mutation, can be easily detected with good sensitivity.

In addition, the method of detecting a mutation according to the present invention may be employed as a method of detecting a mutation in the ALK gene, and may include the below-described processes (I) to (IV), and may further include the below-described process (V). The method of detecting a mutation according to the present invention has a feature of using the above-described mutation detection probe, and other configurations, conditions and the like are not particularly limited by the description below.

Process (I): contacting the mutation detection probe with a single-stranded nucleic acid in a sample, to hybridize the fluorescently-labeled oligonucleotide and the single-stranded nucleic acid, to thereby obtain a hybrid.

Process (II): dissociating the hybrid by changing the temperature of the sample containing the hybrid, and measuring a change in fluorescence signal due to the dissociation of the hybrid.

Process (III): measuring a Tm value, which is the dissociation temperature of the hybrid, based on the change in fluorescence signal.

Process (IV): detecting the presence of the mutation in the ALK gene, based on the Tm value.

Process (V): determining the abundance ratio of single-stranded nucleic acid having the mutation in the total single-stranded nucleic acids contained in the sample, based on the presence of the mutation.

Furthermore, the method according to the present invention may further include amplifying the nucleic acid before the obtainment of the hybrid in the process (I) or simultaneously with the obtainment of the hybrid in the process (I), in addition to the processes (I) to (IV) or in addition to the processes (I) to (V).

The measurement of the Tm value in the process (III) may include not only measuring the dissociation temperature of the hybrid, but also measuring the differential values of the fluorescence signal that changes according to the temperature when the hybrid is melted.

In the present invention, the nucleic acid in a sample may be a single-stranded nucleic acid or a double-stranded nucleic acid. In a case in which the nucleic acid is a double-stranded nucleic acid, the method may include, for example, melting (dissociating) the double-stranded nucleic acid in the sample into single-stranded nucleic acids by heating before being hybridized with the fluorescently labeled probe. The dissociation of a double-stranded nucleic acid into single-stranded nucleic acids enables hybridization with the fluorescently labeled probe.

In the present invention, the nucleic acid contained in the sample to be detected may be, for example, a nucleic acid originally contained in a biological sample, or an amplification product obtained by amplifying a region of the gene of interest that contains a mutated site(s) of the ALK gene by PCR or the like using a nucleic acid originally contained in a biological sample as a template with a view of improving the detection accuracy. The length of the amplification product is not particularly limited, and may be, for example, a length of from 50 mer to 1000 mer, or a length of from 80 mer to 200 mer. Furthermore, the nucleic acid in the sample may be, for example, a cDNA that has been synthesized from RNAs derived from a biological sample (e.g., total RNAs, mRNAs, etc.) by RT-PCR (Reverse Transcription PCR).

In the present invention, the addition ratio (molar ratio) of the mutation detection probe according to the present invention relative to the nucleic acids in the sample is not particularly limited. The amount of the probe to be added may be, for example, no more than 1 fold (by mol) the amount of DNAs in the sample. From the viewpoint of ensuring a sufficient detection signal, the addition ratio of the mutation detection probe according to the present invention to be added relative to the nucleic acids in the sample (in a molar ratio) may be 0.1 or lower.

The "nucleic acids in the sample" may be, for example, a total of nucleic acids to be detected that have the mutation to be detected and nucleic acids, other than the nucleic acids to be detected, that do not have the mutation, or a total of amplification products containing a detection target sequence having the mutation to be detected and amplification products containing a sequence, other than the detection target sequence, that do not have the mutation. Although the ratio of the nucleic acid to be detected relative to nucleic acids in the sample is usually unknown in advance, the consequential addition ratio of the probe relative to the nucleic acids to be detected (or the amplification products containing a sequence to be detected) (in a molar ratio) may be 10 or lower. The addition ratio of the mutation detection probe relative to the nucleic acids to be detected (or the amplification products containing a sequence to be detected) (in a molar ratio) may be 5 or lower, or 3 or lower. The lower limit of the ratio is not particularly limited, and may be, for example, 0.001 or higher, 0.01 or higher, or 0.1 or higher.

The addition ratio of the mutation detection probe according to the present invention relative to DNAs may be, for example, a molar ratio relative to double-stranded nucleic acids or a molar ratio relative to single-stranded nucleic acids.

In the present invention, the measurement of a change in the signal caused by a temperature change for determining a Tm value may be carried out by measuring the absorbance at 260 nm on the basis of the principle described above. However, the measurement may be carried out by measuring a signal which is based on a signal from the label attached to the mutation detection probe, and which varies in accordance with the degree of the formation of a hybrid of a single-stranded DNA and the mutation detection probe. Therefore, the above-described fluorescently labeled oligonucleotide may be used as the mutation detection probe. Examples of the fluorescently labeled oligonucleotide include a fluorescently labeled oligonucleotide of which the fluorescence intensity when the oligonucleotide is hybridized with a target sequence thereof is decreased (quenched) as compared to the fluorescence intensity when the oligonucleotide is not hybridized with the target sequence thereof, and a fluorescently labeled oligonucleotide of which the fluorescence intensity when the oligonucleotide is hybridized with a target sequence thereof is increased as compared to the fluorescence intensity when the oligonucleotide is not hybridized with the target sequence thereof.

The former fluorescently labeled oligonucleotide does not show a fluorescence signal or only a weak fluorescence signal when the fluorescently labeled oligonucleotide forms a hybrid (a double-stranded DNA) with the sequence to be detected; however, the fluorescently labeled oligonucleotide becomes to show a fluorescence signal or shows an increased fluorescence signal when the fluorescently labeled oligonucleotide is dissociated by heating.

The latter fluorescent-labeled oligonucleotide shows a fluorescence signal when the fluorescent-labeled oligonucleotide forms a hybrid (a double-stranded DNA) with the sequence to be detected; however, the fluorescent-labeled oligonucleotide shows a decreased fluorescence signal or ceases to show a fluorescent signal when the fluorescent-labeled oligonucleotide is dissociated by heating. Therefore, similar to the measurement of the absorbance at 260 nm described above, the progress of melting can be monitored, and the Tm value can be determined by detecting the change in the fluorescence signal from the fluorescent label under the conditions specific to the fluorescent label (for example, the fluorescence wavelength thereof).

The method for detecting the change in the signal based on a signal from the fluorescent dye in the mutation detection method according to the present invention is described below by way of specific examples. The mutation detection method according to the present invention has a feature of using the mutation detection probe of the present invention, and other processes and conditions of the method are not limited in any way.

The sample containing a nucleic acid that serves as a template for nucleic acid amplification is not particularly limited as long as the sample contains a nucleic acid, particularly the ALK gene. Examples of such a sample include a sample that is derived from or can be derived from any biological source, examples of which include: a tissue such as colon or lung; a hemocyte such as a leukocyte cell; whole blood; plasma; a sputum; a suspension of oral mucosa; a somatic cell of nail, hair or the like; a germ cell; milk; gascitic fluid; a paraffin-embedded tissue; gastric juice; a gastric lavage fluid; urine; peritoneal fluid; amniotic fluid; and a cell culture. The method for sampling the sample, the method for preparing the sample containing a nucleic acid, and the like are not limited, and, conventional methods known in the art may be employed therefor. A nucleic acid obtained from such a biological source may be directly used as the template, or may be used after the sample has been subjected to pretreatment that modifies the properties of the sample.

For example, in a case in which whole blood is used as the sample, the isolation of genomic DNA from the whole blood may be carried out by a conventional method known in the art. For example, a commercially available genomic DNA isolation kit (trade name: GFX GENOMIC BLOOD DNA PURIFICATION KIT, available from GE Healthcare Biosciences), etc. may be used.

Next, a mutation detection probe including the fluorescently labeled oligonucleotide is added to the sample containing an isolated genomic DNA.

The mutation detection probe may be added to a liquid sample containing an isolated genomic DNA, or may be mixed with a genomic DNA in an appropriate solvent. The solvent is not particularly limited, and examples of the solvent include conventional solvents known in the art, such as: a buffer solution such as Tris-HCl; a solvent containing at least one of KCl, $MgCl_2$, $MgSO_4$, or glycerol; and a PCR reaction solution.

The timing of adding the mutation detection probe is not particularly limited. For example, in a case in which an amplification process such as PCR described below is carried out, the mutation detection probe may be added to the PCR amplification product after the amplification process, or may be added before the amplification process.

In a case in which the mutation detection probe is added before an amplification process such as PCR is carried out, for example, a fluorescent dye or a phosphate group may have been added to the 3' end of the probe, as described above.

The method of amplifying a nucleic acid may be, for example, a method in which a polymerase is employed. Examples thereof include a PCR method, an ICAN method, a LAMP method, and an NASBA method. In a case in which the amplification is carried out by a method in which a polymerase is employed, the amplification may be carried out in the presence of the probe according to the present invention. Those skilled in the art would be able to easily adjust the reaction conditions of the amplification and the like depending on the probe and polymerase to be used. As a result, since the presence or absence of a mutation can be detected by only analyzing the Tm value of the probe after the amplification of the nucleic acid is carried out, it is not necessary to separate the amplification product after completion of the reaction. Thus, contamination by the amplification product does not occur. In addition, since the detection can be carried out using the same apparatus as the apparatus required for the amplification, conveyance of a vessel is unnecessary, and automatization of the process is facilitated.

The DNA polymerase to be used in the PCR method may be selected, without particular limitation, from DNA polymerases that are usually used for PCR. Examples of the DNA polymerase include GENE TAQ (trade name, manufactured by NIPPON GENE CO., LTD.), PRIMESTAR MAX DNA POLYMERASE (trade name, manufactured by Takara Bio Inc.), and a Taq polymerase.

The amount of the polymerase to be used is not particularly limited as long as a usually-applied polymerase concentration is provided. For example, in a case in which a Taq polymerase is used, the concentration of the Taq polymerase may be, for example, a concentration of from 0.01 U to 100 U relative to 50 µl of the reaction solution. In this range, for example, the sensitivity of the detection of mutation in the ALK gene tends to be increased The PCR method may be carried out under the conditions appropriately selected from usually-employed conditions.

When the amplification is carried out, the amplification may be monitored using real-time PCR so that the copy number of the DNA (a sequence to be detected) contained in the sample can be measured. In other words, the proportion of probes forming hybrids is increased as the amplification of the DNA (a sequence to be detected) by PCR proceeds, thereby changing the fluorescence intensity. By monitoring the change in the fluorescence intensity, the copy number and/or the abundance ratio of the sequence to be detected (either a normal DNA or a mutant DNA) contained in the sample can be obtained.

In the mutation detection method according to the present invention, the fluorescent-labeled oligonucleotide and a single-stranded nucleic acid in the sample are brought into contact with each other, thereby allowing hybridization thereof. The single-stranded nucleic acid in the sample may be prepared by, for example, dissociating the PCR amplification product obtained in the above-described manner.

The heating temperature employed for dissociation of the PCR amplification product (the heating temperature in the dissociation process) is not particularly limited as long as it is a temperature at which the amplification product is capable of being dissociated. For example, the heating temperature may be in the range of from 85° C. to 95° C. The heating time is not particularly limited, either. The heating time may be, for example, in the range of from 1 second to 10 minutes, or from 1 second to 5 minutes.

The hybridization of the dissociated single-stranded DNA and the fluorescent-labeled oligonucleotide may be carried out by, for example, decreasing, after the dissociation process, the temperature from the heating temperature employed in the dissociation process. The temperature condition for the hybridization may be, for example, in the range of from 40° C. to 50° C.

The volume and concentration of each component in the reaction solution in the hybridization process are not particularly limited. In regard to specific examples thereof, the concentration of DNAs in the reaction solution may be, for example, a concentration of from 0.01 µM to 1 µM, or a concentration of from 0.1 µM to 0.5 µM. The concentration of the fluorescent-labeled oligonucleotide may be, for example, in a range in which the above-described addition ratio relative to DNAs is satisfied, and may be, for example, a concentration of from 0.001 µM to 10 µM, or a concentration of from 0.001 µM to 1 µM.

The resultant hybrid of the single-stranded DNA and the fluorescent-labeled oligonucleotide is gradually heated, and a change in fluorescence signal caused by the temperature increase is measured. For example, in the case of using Q PROBE®, the fluorescence intensity in the state of being hybridized with the single-stranded DNA is decreased (or quenched) as compared to the fluorescence intensity in the dissociated state. Therefore, for example, the hybrid emitting decreased fluorescence or the quenched hybrid may be gradually heated, and an increase in fluorescence intensity caused by the temperature increase may be measured.

The temperature range in which the change in fluorescence intensity is measured is not particularly limited, and the initial temperature may be, for example, a temperature of from room temperature to 85° C., or a temperature of from 25° C. to 70° C. The final temperature may be, for example, a temperature of from 40° C. to 105° C. The temperature increase rate is not particularly limited, either, and may be, for example, in the range of from 0.1° C./sec to 20° C./sec, or in the range of from 0.3° C./sec to 5° C./sec.

Figure 1B:
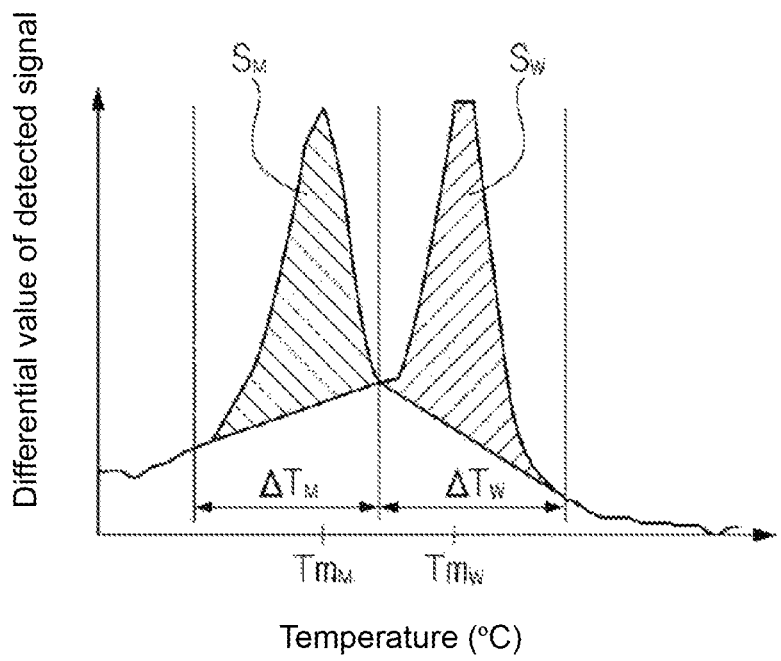
FIG. 1B shows an example of a differential melting curve of the nucleic acid mixture.
Figure 2A:
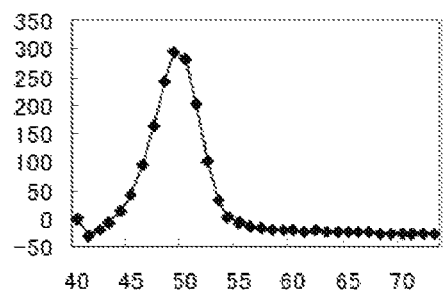
FIGS. 2A and 2B are graphs showing the results of Tm analysis performed for the sample ID: A according to Example 1 of the present invention.
Figure 2B:
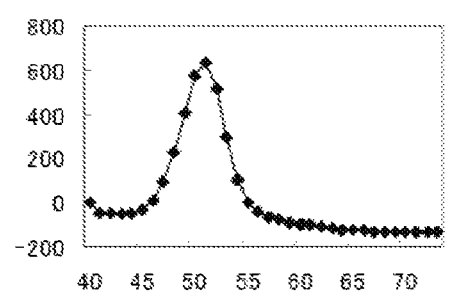
Figure 3A:
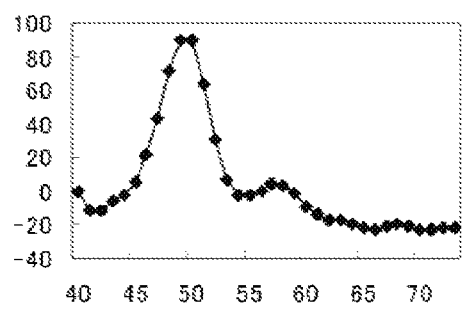
FIGS. 3A and 3B are graphs showing the results of Tm analysis performed for the sample ID: B according to Example 1 of the present invention.
Figure 3B:
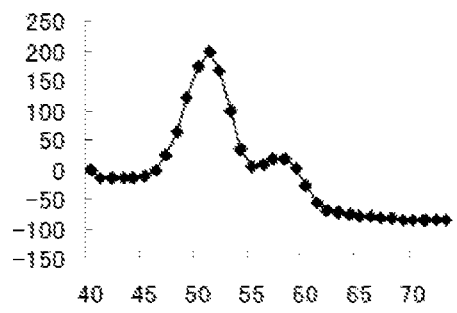
Figure 4A:
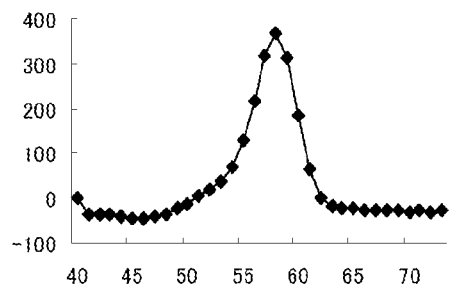
FIGS. 4A and 4B are graphs showing the results of Tm analysis performed for the sample ID: C according to Example 1 of the present invention.
Figure 4B:
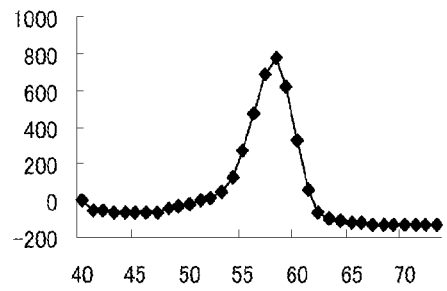

Next, the change in the signal is analyzed to determine the Tm value (see FIGS. 1A and 1B). More specifically, the Tm value may be determined by calculating a differential value at each temperature (−d(Fluorescence Intensity)/dt) from the fluorescent intensity obtained, and taking the temperature at which the differential value takes the lowest value as the Tm value. The Tm value may alternatively be determined as the point at which the increase in fluorescence intensity per unit time ((Increase in Fluorescence Intensity)/t) takes the largest value. On the contrary, in a case in which a probe of which signal intensity is increased by the formation of the hybrid, rather than a quenching probe, is used as the fluorescently labeled probe, the signal analysis and the determination of the Tm value may be carried out by measuring a decrease in fluorescence intensity.

In the present invention, a change in fluorescence signal caused by a temperature increase (preferably an increase in fluorescence intensity) may be measured while heating the hybrid as described above. However, instead of this method, the measurement of a change in signal may alternatively be carried out, for example, in the course of hybrid formation. In other words, the temperature of the sample, to which the probe has been added, may be decreased, and a change in fluorescence signal caused by the temperature decrease may be measured in the course of hybrid formation.

For example, in case in which Q PROBE® is used, the fluorescence intensity is high immediately after the probe is added to the sample since the probe is in the dissociated state. However, when the hybrid is formed by temperature decrease, the fluorescence is decreased (or quenched). Therefore, for example, a decrease in fluorescence intensity caused by temperature decrease may be measured while gradually decreasing the temperature of the heated sample.

On the other hand, in a case in which a fluorescently labeled probe of which signal is increased by hybrid formation is used, the fluorescence intensity is low (or quenched) immediately after the probe is added to the sample since the probe is in the dissociated state. However, when the hybrid is formed by temperature decrease, the fluorescence intensity is increased. Therefore, for example, an increase in fluorescence intensity caused by temperature decrease may be measured while gradually decreasing the temperature of the sample.

The mutation detection method according to the present invention includes detecting at least one of the ALK (L1197M) mutation or the ALK(C1156Y) mutation. That is, the mutation detection method according to the present invention includes any one of the following embodiments:

(1) an embodiment in which only the ALK(L1197M) mutation is detected by using at least one of the P1, P2, P3, P7 and P8 fluorescently labeled oligonucleotides, without using the P4 fluorescently labeled oligonucleotide;

(2) an embodiment in which only the ALK(C1156Y) mutation is detected by using the P4 fluorescently labeled oligonucleotide, without using any of the P1, P2, P3, P7 and P8 fluorescently labeled oligonucleotides; and (3) an embodiment in which both of the ALK(L1197M) and the ALK(C1156Y) mutations are detected by using at least one of the P1, P2, P3, P7 and P8 fluorescently labeled oligonucleotides in combination with the P4 fluorescently labeled oligonucleotide.

The plural mutations in the ALK gene may be detected by the same system or by different systems. In a case in which the plural ALK gene mutations are detected by the same system, the detection method is not particularly restricted. For example, the probes capable of detecting the respective mutations may be pre-mixed and added to a sample, or the probes capable of detecting the respective mutations may be successively added to a sample containing a single-stranded nucleic acid.

The term "system" means an independent reaction system formed with a sample containing a hybrid in which a fluorescently labeled oligonucleotide and a single-stranded nucleic acid are hybridized.

Here, with regard to the preferred embodiments and sequences of the respective probes and primers that can be used in the mutation detection method according to the present invention, the above-described matters relating thereto are applicable.

<Method of Evaluating Drug Efficacy>

The method of evaluating a drug efficacy or tolerance of the present invention includes: detecting a mutation in the ALK gene by the above-described mutation detection method, and evaluating the tolerance to a drug or the efficacy of a drug based on the results of the detected presence or absence of the mutation.

In the mutation detection method, the L1196M mutation or the C1156Y mutation in the ALK gene may be detected easily with a high sensitivity by using the mutation detection probe according to the present invention, and therefore, based on the mutations in the ALK gene, evaluation of a drug may be carried out easily with a high sensitivity.

In addition, evaluation of the tolerance to a drug and the efficacy of a drug may be carried out based on the presence or absence of a mutation in the ALK gene. The method of evaluating the efficacy of a drug of the present invention is useful in, for example, deciding whether the therapeutic strategy of a disease should be shifted so as to increase the dosage of the drug or use another therapeutic agent instead of the drug, based on the presence or absence of a mutation in the ALK gene.

Specific examples of the drug to be evaluated include those anticancer agents that contain an ALK inhibitor as an active ingredient, particularly anticancer agents for lung cancer treatment such as crizotinib.

<Reagent Kit for Mutation Detection>

The reagent kit for detecting a mutation according to the present invention includes the above-described mutation detection probe.

Since the reagent kit for detecting a mutation includes at least one of the above-described mutation detection probes, it is possible to, for example, more easily detect a mutation in the ALK gene.

In addition, the reagent kit in the present invention may further contain a primer for amplifying a base sequence having a region to which the mutation detection probe hybridizes.

This may enable the reagent kit in the present invention to detect a mutation in the ALK gene with good accuracy.

With regard to the probe(s) and primer(s) that may be contained in the reagent kit, the above descriptions may be applied as they are.

In a case in which the reagent kit for detecting a mutation contains two or more fluorescently labeled oligonucleotides as the mutation detection probes, the fluorescently labeled oligonucleotides may be incorporated separately or in the form of a mixture.

Further, in a case in which the mutation detection kit contains two or more of the above-described probes in the form of a mixture or in a case in which the mutation detection kit contains two or more types of probes as separate reagents which are, for example, mixed to be used in the same reaction system, it is preferred that the two or more types of the probes be labeled with fluorescent dyes having different emission wavelengths, respectively.

By using the probes labeled with respectively different fluorescent dyes, detection of the signal from each probe can simultaneously be carried out even in a single reaction system.

Besides the probe and the primers, the reagent kit according to the present invention may further include reagents required for carrying out the nucleic acid amplification in the detection method according to the present invention. The probe, the primers and other reagents may be separately contained, or some of them may be contained in the state of a mixture.

The term "separately contained" may refer to a state in which individual reagents are separated from each other such that the non-contact state therebetween is maintained, and does not necessarily require that the individual reagents be contained in separate containers that can be independently handled.

When the reagent kit includes a primer set for amplifying a base sequence including a base at the mutation site (a region to which the probe can hybridize), detection of the mutation with higher sensitivity, for example, can be achieved.

The reagent kit according to the present invention may further include an instruction manual that describes instructions for the formation of a differential melting curve for a sample containing a nucleic acid to be detected using the mutation detection probe, and for the detection of a mutation in the ALK gene through Tm value analysis based on the differential melting curve, or instructions that describes various reagents that are contained, or may additionally be contained, in the reagent kit.

EXAMPLES

The present invention will now be described in detail by way of examples. However, the present invention is not limited to these examples in any way.

Example 1

Based on the base sequence (SEQ ID NO:1) including an ALK(L1196M) mutation site or the base sequence (SEQ ID NO:3) including an ALK(C1156Y) mutation site, a probe 3PB-ALKL1196M-mt-R1, which is the P1 fluorescently labeled oligonucleotide that is composed of the bases corresponding to the 123rd to the 139th bases of the base sequence indicated in SEQ ID NO:1 and has a fluorescently labeled cytosine corresponding to the 123rd base (SEQ ID NO:5; probe for detection of the ALK(L1196M) mutation), and a probe 3T-ALKC1156Y-mt-F2, which is the P4 fluorescently labeled oligonucleotide that is composed of the bases corresponding to the 235th to the 252nd bases of the base sequence indicated in SEQ ID NO:3 and has a fluorescently labeled cytosine corresponding to the 252nd base (SEQ ID NO:8; probe for detection of the ALK(C1156Y) mutation), were designed and prepared in accordance with a conventional method (see Table 3). Labeling of the cytosine was performed by using Pacific Blue (hereinafter, referred to as "PB") or TAMRA in accordance with a conventional method. The type of the fluorescent dye is shown in the parentheses at the 3'-end of the respective probes. In the base sequences shown in Table 3, the capital letters indicate the respective positions of mutation. The same applies hereinafter.

TABLE 3

| name | sequence(5'→3') | mer | Tm (WT) | Tm (mt) | ∆ | SEQ ID No. |
|---|---|---|---|---|---|---|
| 3PB-ALKL1196M-mt-R1 | gctccaTcaggatgaac-(PB) | 17 | 39.8 | 48.2 | 8.4 | 5 |
| 3T-ALKC1156Y-mt-F2 | ctgaagtgtActctgaac(TAMRA) | 18 | 37.9 | 45.8 | 7.9 | 8 |

Using the reagents shown in Table 4 or 5 and a fully-automated SNP analyzer (trade name: I-DENSY (trademark); manufactured by ARKRAY, Inc.), PCR and Tm analysis were carried out to verify the performance of the probes demonstrated by the respective fluorescently labeled oligonucleotides for detecting a mutation according to the present invention. It is noted here that "%" in Tables 4 and 5 means % by mass (the same applies hereinafter).

The PCR was performed by treating the reaction solution at 95° C. for 60 seconds and then repeating 50 cycles of a 1-second treatment at 95° C. and a 30-second treatment at 61° C.

The Tm analysis was performed by treating the reaction solution at 95° C. for 1 second and then at 40° C. for 60 seconds and subsequently measuring the changes in the fluorescence intensity with time during a period in which the temperature of the solution was raised from 40° C. to 75° C. at a rate of 1° C./3 seconds.

As for the excitation wavelength and the detection wavelength in the Tm analysis, the fluorescent dye, PACIFIC BLUE, had an excitation wavelength of 365 nm to 415 nm and a detection wavelength of 445 nm to 480 nm and the fluorescent dye, TAMRA, had an excitation wavelength of 520 nm to 555 nm and a detection wavelength of 585 nm to 700 nm. Based on these wavelengths, the changes in the fluorescence intensity originating from the respective fluorescently labeled probes were measured.

TABLE 4

<Case in which plasmid was used as template>

| Taq polymerase (manufactured by ARKRAY Inc.) | 1.88U |
|---|---|
| Tris-HCl | 25 mmol/L |
| BSA | 0.20% |
| Glycerol | 4.50% |
| KCl | 45 mmol/L |
| MgCl$_2$ | 1.5 mmol/L |
| dNTP | 0.2 mmol/L |
| ALK C1156Y-F1 | 0.2 μmol/L |
| ALK C1156Y-R4 | 0.8 μmol/L |
| ALK L1196M F-1 | 0.8 μmol/L |
| ALK L1196M R-2 | 0.2 μmol/L |
| 3PB-ALKL1196M-mt-R1 | 0.1 μmol/L |
| 3T-ALKC1156Y-mt-F2 | 0.1 μmol/L |

TABLE 4-continued

<Case in which plasmid was used as template>

| Nucleic acid mixture | 1 μL |
|---|---|
| Amount of reaction solution | 50 μL |

TABLE 5

<Case in which whole blood was used as template>

| Taq polymerase (manufactured by ARKRAY Inc.) | 1.88U |
|---|---|
| Tris-HCl | 25 mmol/L |
| BSA | 0.20% |
| Glycerol | 4.50% |
| KCl | 45 mmol/L |
| MgCl2 | 1.5 mmol/L |
| dNTP | 0.2 mmol/L |
| ALK C1156Y-F1 | 0.2 μmol/L |
| ALK C1156Y-R4 | 0.8 μmol/L |
| ALK L1196M F-1 | 0.8 μmol/L |
| ALK L1196M R-2 | 0.2 μmol/L |
| 3PB-ALKL1196M-mt-R1 | 0.1 μmol/L |
| 3T-ALKC1156Y-mt-F2 | 0.1 μmol/L |
| Pre-treated whole blood | 4 μL |
| Amount of reaction solution | 50 μL |

<Nucleic Acid Mixture>

Nucleic acid mixtures containing plasmids (Mt(L1196M), Wt(L1196M), Mt(C1156Y) and Wt(C1156Y)) at a prescribed ratio were prepared. The plasmids were obtained by inserting the nucleic acid sequences indicated in SEQ ID NOs:18 to 21 (see Table 6) that include a sequence corresponding to the site of the ALK(L1196M) mutation or ALK (C1156Y) mutation to the EcoRV site of pUC57, respectively, and then treating the resultants with EcoRI. Table 7 shows the content ratios of the plasmids (the number of copies per 1 μL) in the respective nucleic acid mixtures of samples A to C.

<Pre-Treated Whole Blood>

After adding 10 μl of whole blood to 70 μl of a diluent 1 and thoroughly mixing the resultant, 10 μl of the thus-obtained mixture was added to 70 μl of a diluent 2. Then, 17 μl of the resulting mixture was heated at 95° C. for 10 minutes, thereby obtaining a pre-treated whole blood in an amount of 4 μl. The entire amount of 4 μl of the pre-treated whole blood was added to the reaction solution. The compositions of the diluents 1 and 2 are as shown in Table 8.

TABLE 6

| Plasmid name | sequence(5'→3') | mer | SEQ ID No |
|---|---|---|---|
| Mt ALK (L1196M) | agtttaagatttgcccagactcagctcagttaattttggttacatccctctctgctctgcagcaaattcaaccaccag aacattgttcgctgcattggggtgagcctgcaatccctgccccggttcatcctgAtggagctcatggcgggggaga cctcaagtccttcctccgagagacccgccctcgcccggtgagtgagaaccagtctttgctgcagttgttgtgccaag gacaggagcaaggatggaaggagcaagagtgggcagcctgggtagcaagttcctcgatggaacccagg | 300 | 18 |
| Wt ALK (L1196M) | agtttaagatttgcccagactcagctcagttaattaggttacatccctctctgctctgcagcaaattcaaccaccag aacattgttcgctgcattggggtgagcctgcaatccctgccccggttcatcctgCtggagctcatggcgggggaga | 300 | 19 |

TABLE 6 -continued

| Plasmid name | sequence(5'→3') | mer | SEQ ID No |
|---|---|---|---|
| | cctcaagtccttcctccgagagacccgccctcgccggtgagtgagaaccagtctttgctgcagttgttgtgccaa ggacaggagcaaggatggaaggagcaagagtgggcagcctgggtagcaagttcctcgatggaacccagg | | |
| Mt ALK (C1156Y) | gtccggaatgcccaacgacccaagccaagcccctgcaagtggctgtgaaggtaagaagtggctcactcttgagcc tgcccttggcttgcggactctgttaggctgcagttctcagctcacagcctcctcctcctcccaccctcccttct ctgcccagacgctgcctgaaggtActctgaacaggacgaactggatttcctcatggaagccctgatcatcaggtaa agccacagagagacaocctcaccccaactcccctctgccccaaagaacctggagaggtttctaacagatcg | 300 | 20 |
| Wt ALK (C1156Y) | gtccggaatgcccaacgacccaagccaagcccctgcaagtggctgtgaaggtaagaagtggctcactcttgagcc tgcccttggcttgcggactctgtaggctgcagttctcagctcacagcctcctcctcctcccaccctcccttct ctgcccagacgctgcctgaaggtGctctgaacaggacgaactggatttcctcatggaagccctgatcatcaggta aagccacagagagacaccctcaccccaactcccctctgccccaaagaacctggagaggtttctaacagatcg | 300 | 21 |

TABLE 7

| Mutation ID | content | WT (L1196M) sample | WT(C1156Y) sample | mt (L1196M) sample | mt (C1156Y) sample |
|---|---|---|---|---|---|
| A | WT | 1000 | 1000 | 0 | 0 |
| B | mt 10% | 900 | 900 | 100 | 100 |
| C | mt 100% | 0 | 0 | 1000 | 1000 |

TABLE 8

| Diluent 1 | | Diluent 2 | |
|---|---|---|---|
| Tris-HCl (pH 8.0) | 10 mM | Tris-HCl (pH 8.0) | 10 mM |
| EDTA (pH 8.0) | 0.1 mM | 500 mM EDTA (pH 8.0) | 0.1 mM |
| SDS | 0.30% | | |

Figure 5A:
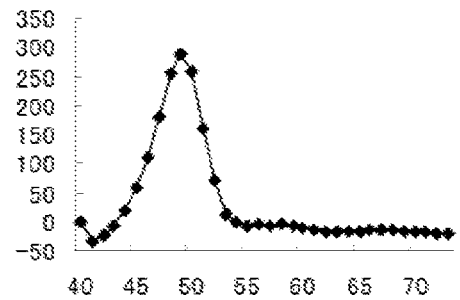
FIGS. 5A and 5B are graphs showing the results of Tm analysis performed for the whole blood sample according to Example 1 of the present invention.
Figure 5B:
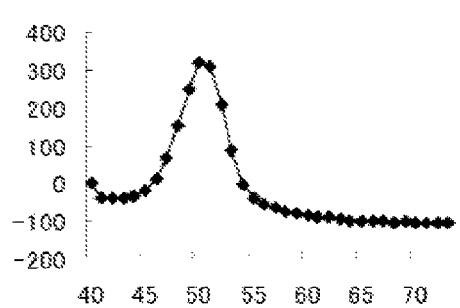

Based on the result of the Tm analysis, FIGS. 2A to 5B showing the changes in the fluorescence value of the respective probes were obtained. FIGS. 2A to 4B show the results obtained by using the nucleic acid mixture-containing sample IDs: A to C, respectively. FIGS. 5A and 5B show the results obtained by using a whole blood as a sample. FIGS. 2A, 3A, 4A and 5A show the presence or absence of the ALK (L1196M) mutation, and FIGS. 2B, 3B, 4B, and 5B show the presence or absence of the ALK(C1156Y) mutation. In the figures, the ordinate represents the change in the fluorescence intensity per unit time (increase in the d-Fluorescence intensity/t) and the abscissa represents the temperature (° C.).

As a result, in FIGS. 2A, 3A, 4A, and 5A in which the ALK(L1196M) mutation was detected, a peak was observed at 49° C. the wild-type (C/C) sample and a peak was observed at 58° C. for the mutant-type (A/A) sample. In FIGS. 2B, 3B, 4B, and 5B in which the ALK(C1156Y) mutation was detected, a peak was observed at 51° C. for the wild-type (G/G) sample and a peak was observed at 58° C. the mutant-type (A/A) sample. As for the sample solution B in which a mutant-type and wild-type were mixed, peaks derived from the ALK(L1196M) mutation and a peak derived from the ALK(C1156Y) mutation, respectively, were both observed at 58° C. (see FIGS. 3A and 3B).

Further, it was revealed that the ALK(L1196M) and ALK (C1156Y) mutations can be easily detected at the same time even when a blood specimen is used as the test sample.

Therefore, it was demonstrated that the ALK(L1196M) and ALK(C1156Y) mutations can be simultaneously detected by using the fluorescently labeled oligonucleotides according to the present invention as probes.

Example 2

As a probe for detecting the ALK(L1196M) mutation, based on the base sequence (SEQ ID NO:1) including an ALK(L1196M) mutation site, a probe 3T-ALKL1196M-mt-F7, which is the P2 fluorescently labeled oligonucleotide that is composed of the bases corresponding to the 123rd to the 141st bases of the base sequence indicated in SEQ ID NO:1 and has a fluorescently labeled cytosine corresponding to the 141st base, was designed and prepared in accordance with a conventional method (see Table 9). Labeling of the cytosine was performed using TAMRA in accordance with a conventional method.

A primer ALK L1196M-mt-F10, which is one example the P5 primer having a base corresponding to the 133rd base of the sequence indicated in SEQ ID NO:1, and a primer ALK L1196M-WT-F6, which is the P6 primer having a base corresponding to the 133rd base of the sequence indicated in SEQ ID NO:2 as well as a mismatch base, were designed based on the base sequences indicated in SEQ ID NOs:1 and 2, respectively, and these primers were prepared in accordance with a conventional method (see Table 10). It is noted that, in Table 10, the underlined base represents the mismatch base. Further, based on the sequence indicated in SEQ ID NO:1, a reverse primer, ALK L1196M R-3, was designed and prepared in accordance with a conventional method (see Table 10).

TABLE 9

| name | sequence(5'→3') | mer | Tm (WT) | Tm (mt) | Δ | SEQ ID No. |
|---|---|---|---|---|---|---|
| 3T-ALKL1196M-mt-F7 | gttcatcctgAtggagctc-(TAMRA) | 19 | 48.1 | 51.3 | 3.3 | 6 |

TABLE 10

| name | sequence (5'→3') | mer | SEQ. ID No. |
|---|---|---|---|
| ALK L1196M-mt-F10 | tgcatcaccctgccccggttcatcctgA | 28 | 14 |
| ALK L1196M-WT-F6 | ctacgacctgccccggttcaacctgC | 26 | 15 |
| ALK L1196M R-3 | ggacggacggaccttggcacaacaactgcagcaaagac | 38 | 17 |

Using the reagents shown below and a fully-automated SNP analyzer (trade name: I-DENSY (trademark); manufactured by ARKRAY, Inc.), PCR and Tm analysis were carried out to verify the performance of the probes demonstrated by the respective fluorescently labeled oligonucleotides for detecting a mutation according to the present invention.

The PCR was performed by treating the reaction solution at 95° C. for 60 seconds and then repeating 50 cycles of a 1-second treatment at 95° C. and a 15-second treatment at 52° C.

The Tm analysis was performed after the PCR by treating the reaction solution at 95° C. for 1 second and then at 40° C. for 60 seconds and subsequently measuring the changes in the fluorescence intensity with time during a period in which the temperature of the solution was raised from 40° C. to 75° C. at a rate of 1° C./3 seconds. In the Tm analysis, the excitation wavelength was from 520 nm to 555 nm, and the detection wavelength was from 585 nm to 700 nm (TAMRA). Based on these wavelengths, the changes in the fluorescence intensity originating from the respective fluorescently labeled probes were measured.

TABLE 11

<Case in which plasmid was used as template>

| | |
|---|---|
| Taq polymerase (manufactured by ARKRAY Inc.) | 1.88U |
| Tris-HCl | 25 mmol/L |
| BSA | 0.20% |
| Glycerol | 4.50% |
| KCl | 45 mmol/L |
| MgCl2 | 1.5 mmol/L |
| dNTP | 0.2 mmol/L |
| 100 uM 3T-ALKL1196M-mt-F7 | 0.4 μmol/L |
| 100 uM ALK L1196M-WT-F6 | 0.25 μmol/L |
| 100 uM ALK L1196M-mt-F10 | 0.25 μmol/L |
| 100 uM ALK L1196M R-3 | 2 μmol/L |
| Nucleic acid mixture | 1 μL |
| Amount of reaction solution | 50 μL |

<Nucleic Acid Mixture>

Nucleic acid mixtures containing the same plasmid used in Example 1, that is, Mt(L1196M) or Wt(L1196M), respectively, were prepared. Table 12 shows the content ratio of the plasmid (the number of copies per 1 μL) in the respective nucleic acid mixtures of samples D to G.

TABLE 12

| ID | Mutation content | WT(L1196M) sample | mt(L1196M) sample |
|---|---|---|---|
| D | WT | 20000 | 0 |
| E | mt 0.3% | 19940 | 60 |

TABLE 12-continued

| ID | Mutation content | WT(L1196M) sample | mt(L1196M) sample |
|---|---|---|---|
| F | mt 1% | 19800 | 200 |
| G | mt 100% | 0 | 20000 |

Figure 6A:
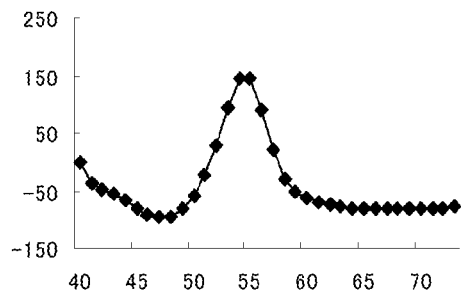
FIGS. 6A to 6D are graphs showing the results of Tm analysis according to Example 2 of the present invention.
Figure 6B:
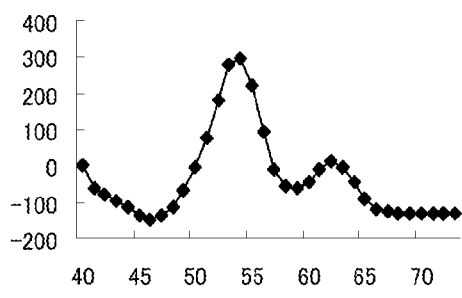
Figure 6C:
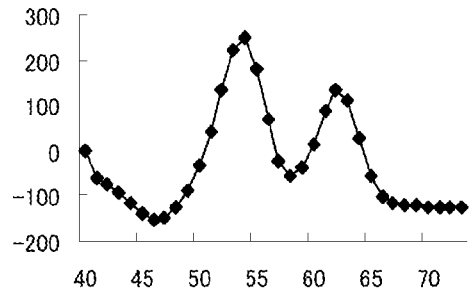
Figure 6D:
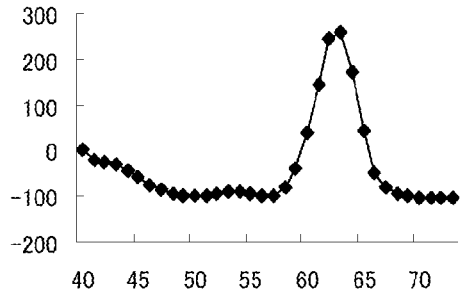

Based on the Tm analysis, FIGS. 6A to 6D showing the changes in the fluorescence value of the respective probes were obtained. FIG. 6A shows the result obtained by using the sample D; FIG. 6B shows the result obtained by using the sample E; FIG. 6C shows the result obtained by using the sample F; and FIG. 6D shows the result obtained by using the sample G. In FIGS. 6A to 6D, the ordinate represents the change in the fluorescence intensity per unit time (increase in the d-fluorescence intensity/t) and the abscissa represents the temperature (° C.).

As shown in FIGS. 6A to 6D, a peak was observed at 54° C. for the wild-type (C/C) sample and a peak was observed at 63° C. for the mutant-type (A/A) sample.

Therefore, it was revealed that, by using the fluorescently labeled oligonucleotide according to the present invention as a probe in combination with a primer containing a mismatch base (in this Example, a primer for amplifying the wild-type nucleic acid sequence), the presence or absence of the ALK (L1196M) mutation can be easily and highly specifically detected even when the content of the mutation is 0.3% (mt 0.3%, 20,000 cp/test).

Comparative Example 1

Based on the base sequence (SEQ ID NO:1) containing the ALK(L1196M) mutation, a probe 3PB-ALKL1196M-mt-F1 (SEQ ID NO:22) composed of the bases corresponding to the 129th to the 141st bases of the base sequence indicated in SEQ ID NO:1, in which the base corresponding to the 140th base is other than cytosine and the cytosine at the 5'-end is fluorescently labeled, was designed and prepared in accordance with a conventional method (see Table 13).

As template nucleic acids, template oligonucleotides (wild-type: SEQ ID NO:23, and a mutant-type: SEQ ID NO:24) which have a base sequence complementary to the base sequence indicated in SEQ ID NO:1 or 2 were used. The sequences of the template oligonucleotides are shown in Table 14. As samples, a sample containing the wild-type template oligonucleotide, a sample containing the mutant-type template oligonucleotide and a sample containing a 1:1 mixture (molar ratio, the same applies hereinafter) of the wild-type and mutant-type template oligonucleotides were used.

TABLE 13

| name | sequence (5'→3') | mer | GC | Tm (wt:C) | Tm (mt:A) | Δ | SEQ. ID No. |
|---|---|---|---|---|---|---|---|
| 3PB-ALKL1196M-mt-F1 | (PB)-cctgAtggagctc-P | 13 | 61.5 | 34 | 40.5 | 6.5 | 22 |

TABLE 14

| name | sequence(5'→3') | mer | SEQ.ID. No. |
|---|---|---|---|
| WT | atgagctccaGcaggatgaaccggggc | 27 | 23 |
| Mt | atgagctccaTcaggatgaaccggggc | 27 | 24 |

Using the reagents shown below and a fully-automated SNP analyzer (trade name: I-DENSY (trademark); manufactured by ARKRAY, Inc.), Tm analysis was carried out to verify the performance of the probe 3PB-ALKL1196M-mt-F1. The Gene Taq Universal buffer shown in Table 15 was a buffer manufactured by Nippon Gene Co., Ltd. The nucleic acid mixture was adjusted to have a template oligonucleotide concentration of 5 μM, and then 4 μL of the nucleic acid mixture was added to the reaction solution.

The Tm analysis was performed by treating the reaction solution at 95° C. for 1 second and then at 40° C. for 60 seconds and subsequently measuring the changes in the fluorescence intensity with time during a period in which the temperature of the solution was raised from 40° C. to 75° C. at a rate of 1° C./3 seconds. In the Tm analysis, the excitation wavelength was from 365 nm to 415 nm, and the detection wavelength was from 445 nm to 480 nm (PB). Based on these wavelengths, the changes in the fluorescence intensity originating from the fluorescently labeled probe were measured.

TABLE 15

| (Amount of reaction solution: 50 μl) | |
|---|---|
| 1 × Gene Taq Universal buffer× | |
| 3PB-ALKL1196M-mt-F1 | 0.4 μM |
| Nucleic acid mixture | 0.4 μM |

Figure 7:
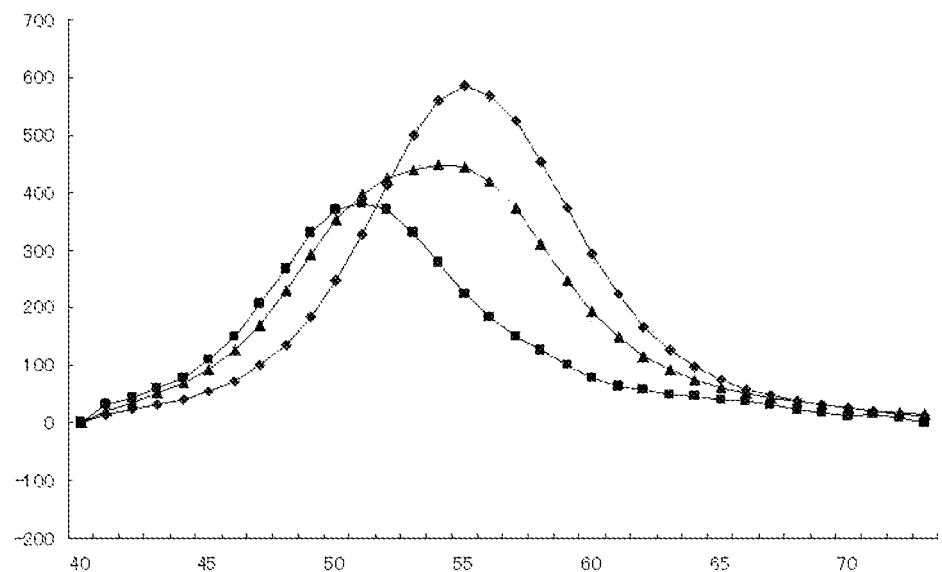
FIG. 7 is a graph showing the result of Tm analysis according to Comparative Example 1 in the present invention.

Based on the Tm analysis, FIG. 7 showing the changes in the fluorescence value of the probes was obtained. In FIG. 7, the ordinate represents the change in the fluorescence intensity per unit time (increase in the d-fluorescence intensity/t) and the abscissa represents the temperature (° C.). In FIG. 7, the pattern indicated with squares represents the results obtained by using the wild-type template oligonucleotide as the template nucleic acid; the pattern indicated with lozenges represents the results obtained by using the mutant-type template oligonucleotide as the template nucleic acid; and the pattern indicated with triangles represents the results obtained by using the 1:1 mixture of the wild-type and mutant-type template oligonucleotides as the template nucleic acid.

In FIG. 7, a peak was observed at 51° C. for the wild-type sample and a peak was observed at 55° C. for the ALK (L1196M) mutant-type sample. Comparing the sample containing 100% wild-type nucleic acid and the sample containing 100% ALK(L1196M) mutant-type nucleic acid, the difference in Tm values was merely 4° C. unlike the calculated values, and it was difficult to visually distinguish the peaks from one another.

Furthermore, when the 1:1 mixture of the mutant-type and wild-type template oligonucleotides was used as the template nucleic acid, only one broad peak was observed at 54° C., and it was not able to detect the ALK(L1196M) mutation.

Comparative Example 2

Based on the base sequence (SEQ ID NO:1) containing the ALK(L1196M) mutation, a probe 5T-ALK-L1196M-mt-F5 (SEQ ID NO:25) composed of the bases corresponding to the 126th to the 142nd bases of the base sequence indicated in SEQ ID NO:1, in which the cytosine at the 5'-end which was not the base corresponding to the 141st base was fluorescently labeled, was designed and prepared in accordance with a conventional method (see Table 16).

TABLE 16

| name | sequence(5'→3') | mer | GC | Tm (wt: C) | Tm (mt: A) | Δ | SEQ. ID No. |
|---|---|---|---|---|---|---|---|
| 5T-ALK-L1196-mt-F5 (TAMRA) | catcctgAtggagctca-P | 17 | 52.9 | 45 | 49 | 4 | 25 |

Using the reagents shown in Table 17 below and a fully-automated SNP analyzer (trade name: I-DENSY (trademark); manufactured by ARKRAY, Inc.), PCR and Tm analysis were carried out to verify the performance of the probe 5T-ALK-L1196M-mt-F5. As the template nucleic acid, a nucleic acid mixture containing the same plasmids used in Example 1 was used. The copy numbers of the respective plasmids in the nucleic acid mixture are as shown in Table 18.

The PCR was performed by treating the reaction solution at 95° C. for 60 seconds and then repeating 50 cycles of a 1-second treatment at 95° C. and a 15-second treatment at 52° C. As the primers, the same primers as those used in Example 2 were employed.

The Tm analysis was performed by treating the reaction solution at 95° C. for 1 second and then at 40° C. for 60 seconds and subsequently measuring the changes in the fluorescence intensity with time during a period in which the temperature of the solution was raised from 40° C. to 75° C. at a rate of 1° C./3 seconds.

In the Tm analysis, the excitation wavelength was from 520 nm to 555 nm, and the detection wavelength was from 585 nm to 700 nm (TAMRA). Based on these wavelengths, the changes in the fluorescence intensity originating from the fluorescently labeled probe were measured.

TABLE 17

| <Case in which plasmid was used as template> | |
|---|---|
| Taq polymerase (manufactured by ARKRAY Inc.) | 1.88U |
| Tris-HCl | 25 mmol/L |
| BSA | 0.20% |
| Glycerol | 4.50% |
| KCl | 45 mmol/L |
| MgCl2 | 1.5 mmol/L |
| dNTP | 0.2 mmol/L |
| 100 uM 5T-ALK-L1196M-mt-F5 | 0.4 μmol/L |
| 100 uM ALK L1196M-WT-F6 | 0.25 μmol/L |
| 100 uM ALK L1196M-mt-F10 | 0.25 μmol/L |
| 100 uM ALK L1196M R-3 | 2 μmol/L |
| Nucleic acid mixture | 1 μL |
| Amount of reaction solution | 50 μL |

TABLE 18

| Mutation content | WT(L1196M) sample | Mt(L1196M) sample |
|---|---|---|
| mt 50% | 1000 | 1000 |

Figure 8:
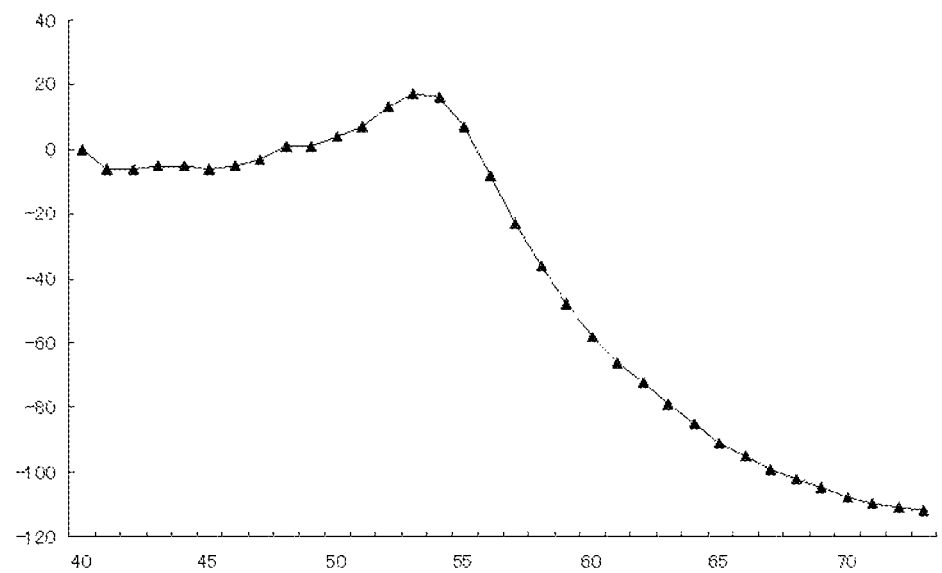
FIG. 8 is a graph showing the result of Tm analysis according to Comparative Example 2 in the present invention.

Based on the result of the Tm analysis, FIG. 8 showing the changes in the fluorescence value of the probe was obtained. In the figure, the ordinate indicates the change in the fluorescence intensity per unit time (increase in the d-fluorescence intensity/t), and the abscissa indicates the temperature (° C.).

As shown in Table 8, even when the mismatch base-containing primer used in Example 2 for high-sensitive detection was employed, only one peak was observed at 54° C., and it was not able to detect the ALK(L1196M) mutation.

Comparative Example 3

Based on the base sequence (SEQ ID NO:3) containing the ALK(C1156Y) mutation, a probe 3T-ALK-C1156Y-mt-F4 (SEQ ID NO:26) composed of the bases corresponding to the 229th to the 245th bases of the base sequence indicated in SEQ ID NO:3, in which the cytosine at the 3'-end which was not the base corresponding to the 252nd base of SEQ ID NO:3 was fluorescently labeled, was designed and prepared in accordance with a conventional method (see Table 19).

As template nucleic acids, template oligonucleotides (wild-type: SEQ ID NO:27, and mutant-type: SEQ ID NO:28) which have a base sequence complementary to the base sequence indicated in SEQ ID NO:3 or 4 were used. The sequences of the template oligonucleotides are shown in Table 20. As samples, a sample containing the wild-type template oligonucleotide, a sample containing the mutant-type template oligonucleotide and a sample containing a 1:1 mixture of the wild-type and mutant-type template oligonucleotides were used.

Tm analysis was carried out to verify the performance of the probe in the same manner as in Comparative Example 1, except that the above-described probe and template nucleic acids were used and that the excitation wavelength and the detection wavelength were from 520 nm to 555 nm and from 585 nm to 700 nm, respectively.

TABLE 19

| name | sequence(5'→3') | mer | SEQ. ID No. |
|---|---|---|---|
| 3T-ALK-C1156Y-mt-F4 | cgctgcctgaagtgtAc-(TAMRA) | 17 | 26 |

TABLE 20

| sequence(5'→3') | mer | SEQ. ID No. |
|---|---|---|
| gttcagagCacacttcaggcagcgtct | 27 | 27 |
| gttcagagTacacttcaggcagcgtct | 27 | 28 |

Figure 9:
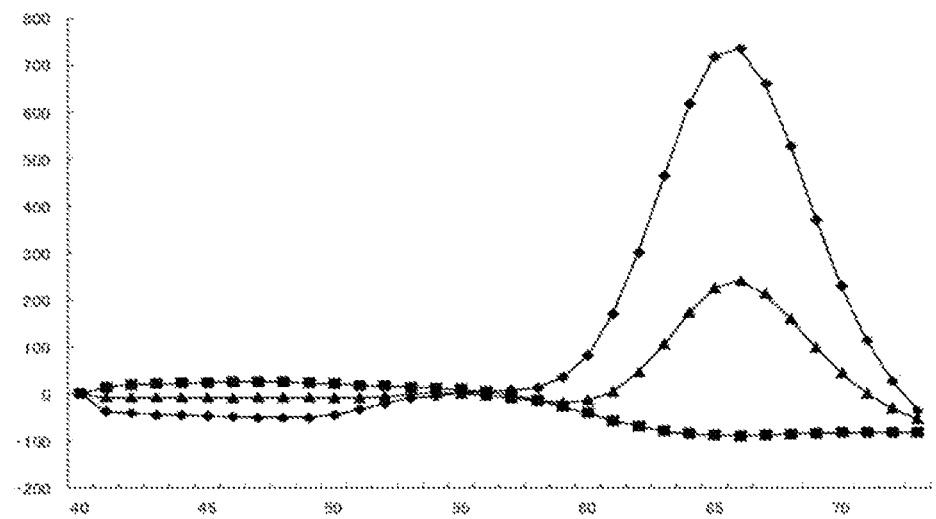
FIG. 9 is a graph showing the result of Tm analysis according to Comparative Example 3 in the present invention.

Based on the Tm analysis, FIG. 9 showing the changes in the fluorescence value of the respective probes was obtained. In FIG. 9, the ordinate indicates the change in the fluorescence intensity per unit time (increase in the d-fluorescence intensity/t), and the abscissa indicates the temperature (° C.). In FIG. 9, the pattern indicated with lozenges represents the results obtained by using the wild-type template oligonucleotide as the template nucleic acid; the pattern indicated with squares represents the results obtained by using the mutant-type template oligonucleotide as the template nucleic acid; and the pattern indicated with triangles represents the results obtained by using a 1:1 mixture of the wild-type and mutant-type template oligonucleotides as the template nucleic acid.

In FIG. 9, although a peak derived from the ALK(C1156Y) mutant-type nucleic acid was observed at 66° C., no peak was derived from the wild-type nucleic acid and only one peak was detected for the sample containing the mixture of the wild-type and mutant-type nucleic acids. Thus, it was not able to detect the ALK(C1156Y) mutation.

Example 3

As a probe for detecting the ALK(L1196M) mutation, based on the wild-type base sequence (SEQ ID NO:2), a probe 5T-ALK-L1196M-R1 (SEQ ID NO:7), which is the P3 fluorescently labeled oligonucleotide that is composed of the bases corresponding to the 123rd to the 138th bases of the base sequence indicated in SEQ ID NO:2 and has a fluorescently labeled cytosine corresponding to the 138th base, was designed and prepared in accordance with a conventional method (see Table 21). Labeling of the cytosine was performed in accordance with a conventional method.

As template nucleic acids, template oligonucleotides (wild-type: SEQ ID NO:29, and mutant-type: SEQ ID NO:30) which have a base sequence complementary to the base sequence indicated in SEQ ID NO:1 or 2 were used. The sequences of the template oligonucleotides are shown in Table 22. As samples, a sample containing the wild-type template oligonucleotide, a sample containing the mutant-type template oligonucleotide and a sample containing a 1:1 mixture of the wild-type and mutant-type template oligonucleotides were used.

Tm analysis was carried out in the same manner as in Example 1, except that the above-described probe and template nucleic acids were used and that the changes in the fluorescence intensity originating from the fluorescently labeled probe were measured with an excitation wavelength of from 520 nm to 555 nm and a detection wavelength of from 585 nm to 700 nm.

It is noted that, in Table 22, "S" and "Y" are bases corresponding to a mutation site other than the ALK(L1196M) mutation, respectively, and "S" represents "g or c" and "Y" represents "t or c".

TABLE 21

| name | sequence(5'→3') | mer | GC | Tm (wt: C) | Tm (mt: A) | Δ | SEQ. ID No. |
|---|---|---|---|---|---|---|---|
| 5T-ALK-L1196M-R1 | (TAMRA)-ctccaGcaggatgaac-P | 16 | 56 | 47.4 | 39.2 | 8.2 | 7 |

TABLE 22

| name | sequence(5'→3') | mer | SEQ. ID No. |
|---|---|---|---|
| ALK-WT-F | ccSgttcatcctgCtggagctYatg | 25 | 29 |
| ALK-mt-F | ccSgttcatcctgAtggagctYatg | 25 | 30 |

Figure 10:
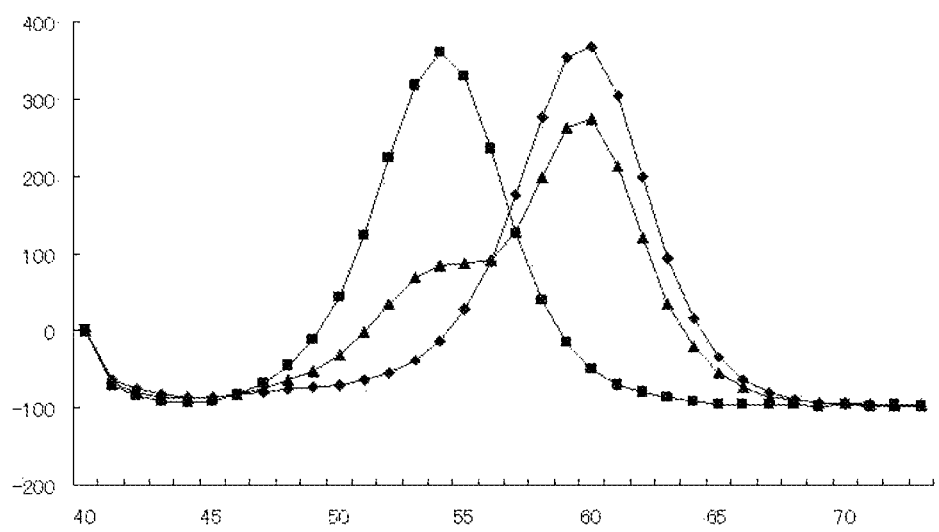
FIG. 10 is a graph showing the result of Tm analysis according to Example 3 of the present invention.

Based on the Tm analysis, FIG. 10 showing the changes in the fluorescence value of the respective probes was obtained. In FIG. 10, the ordinate indicates the change in the fluorescence intensity per unit time (increase in the d-fluorescence intensity/t), and the abscissa indicates the temperature (° C.). In FIG. 10, the pattern indicated with lozenges represents the results obtained by using the wild-type template oligonucleotide as the template nucleic acid: the pattern indicated with squares represents the results obtained by using the mutant-type template oligonucleotide as the template nucleic acid; and the pattern indicated with triangles represents the results obtained by using the 1:1 mixture of the wild-type and mutant-type template oligonucleotides as the template nucleic acid.

In FIG. 10, a peak was observed at 60° C. for the wild-type sample, and a peak was observed at 54° C. for the ALK (L1196M) mutant-type sample. Two distinguishable peaks were also observed at 54° C. and 60° C. for the sample of 1:1 mixture of the wild-type and mutant-type nucleic acids. Thus, it was able to sufficiently detect the presence or absence of the ALK(L1196M) mutation.

Comparative Example 4

Based on the wild-type base sequence (SEQ ID NO:2), a probe 3T-ALK-L1196M-F5 (SEQ ID NO:31) composed of the bases corresponding to the 123rd to the 139th bases of the base sequence indicated in SEQ ID NO:2, in which the base corresponding to the 138th base is other than cytosine and the cytosine at the 5'-end is fluorescently labeled, was designed and prepared in accordance with a conventional method (see Table 23).

As template nucleic acids, template oligonucleotides (wild-type: SEQ ID NO:32, and mutant-type: SEQ ID NO:33) which have a base sequence complementary to the base sequence indicated in SEQ ID NO:1 or 2 were used. The sequences of the template oligonucleotides are shown in Table 24. As samples, a sample containing the wild-type template oligonucleotide, a sample containing the mutant-type template oligonucleotide and a sample containing a 1:1 mixture of the wild-type and mutant-type template oligonucleotides were used.

Tm analysis was carried out to verify the performance of the probe in the same manner as in Example 3, except that the above-described probe and template nucleic acids were used.

TABLE 24

| name | sequence(5'→3') | mer | SEQ. ID No. |
|---|---|---|---|
| ALKL1196MWTR | atgagctccaGcaggatgaaccggggc | 27 | 32 |
| ALKL1196MmtR | atgagctccaTcaggatgaaccggggc | 27 | 33 |

Figure 11:
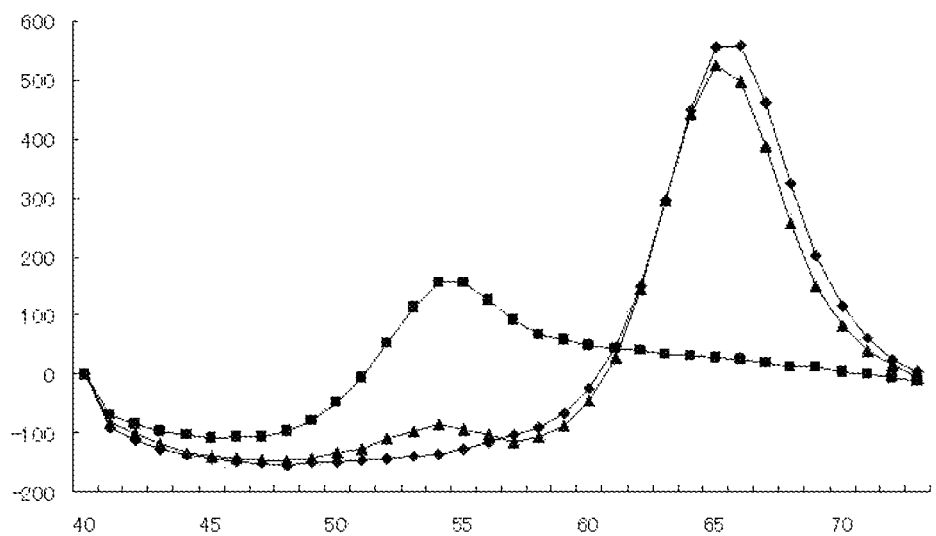
FIG. 11 is a graph showing the result of Tm analysis according to Comparative Example 4 in the present invention.

Based on the Tm analysis, FIG. 11 showing the changes in the fluorescence value of the respective probes was obtained. In FIG. 11, the ordinate indicates the change in the fluorescence intensity per unit time (increase in the d-fluorescence intensity/t), and the abscissa indicates the temperature (° C.). In FIG. 11, the pattern indicated with lozenges represents the results obtained by using the wild-type template oligonucleotide as the template nucleic acid: the pattern indicated with squares represents the results obtained by using the mutant-type template oligonucleotide as the template nucleic acid; and the pattern indicated with triangles represents the results obtained by using the 1:1 mixture of the wild-type and mutant-type template oligonucleotides as the template nucleic acid.

In FIG. 11, a peak was observed at 66° C. for the wild-type sample, and a peak was observed at 55° C. for the mutant-type sample. Meanwhile, in a case in which the sample containing the 1:1 mixture of the wild-type and mutant-type nucleic acids was used, the reactivity of the probe was weak, and it was difficult to sufficiently detect a peak showing the mutation.

Examples 4 and 5

As a probe for detecting the ALK(L1196M) mutation used in Example 4, based on the mutant-type base sequence (SEQ ID NO:1), a probe 5T-ALK-L1196M-mtR5 (SEQ ID NO:9), which is the P7 fluorescently labeled oligonucleotide that is composed of the bases corresponding to the 129th to the 145th bases of the base sequence indicated in SEQ ID NO:1 and has a fluorescently labeled cytosine corresponding to the 145th base, was designed and prepared in accordance with a conventional method (see Table 25). Labeling of the cytosine was performed in accordance with a conventional method.

As template nucleic acids, template oligonucleotides (wild-type: SEQ ID NO:34, and mutant-type: SEQ ID NO:35) which have a base sequence complementary to the base sequence indicated in SEQ ID NO:1 or 2 were used. The sequences of the template oligonucleotides are shown in Table 26. As samples, a sample containing the wild-type template oligonucleotide, a sample containing the mutant-type template oligonucleotide and a sample containing a 1:1 mixture of the wild-type and mutant-type template oligonucleotides were used.

TABLE 23

| name | sequence(5'→3') | mer | GC | Tm (wt: C) | Tm (mt: A) | Δ | SEQ. ID No. |
|---|---|---|---|---|---|---|---|
| 3T-ALK-L1196M-F5 | gttcatcctgCtggagc-(TAMRA) | 17 | 58.8 | 51.4 | 39.8 | 11.6 | 31 |

TABLE 25

| name | sequence(5'→3') | Tm (WT: C) | Tm (mt: A) | ∆ | SEQ. ID No. |
|---|---|---|---|---|---|
| 5T-ALKL1196M-mtR5 | (TAMRA)-ccatgagctccatcagg-P | 41 | 46 | 4.6 | 9 |

TABLE 26

| name | sequence(5'→3') | SEQ. ID No. |
|---|---|---|
| ALK WT2souhosa1306 | tcctgCtggagctcatggc | 34 |
| ALK mt2souhosa1306 | tcctgAtggagctcatggc | 35 |

Further, as a probe for detecting the ALK(L1196M) mutation used in Example 5, based on the wild-type base sequence (SEQ ID NO:2), a probe 3T-ALK-L1196M-WTF12 (SEQ ID NO:10), which is the P8 fluorescently labeled oligonucleotide that is composed of the bases corresponding to the 129th to the 146th bases of the base sequence indicated in SEQ ID NO:2 and has a fluorescently labeled cytosine corresponding to the 146th base, was designed and prepared in accordance with a conventional method (see Table 27). Labeling of the cytosine was performed in accordance with a conventional method.

As template nucleic acids, template oligonucleotides (wild-type: SEQ ID NO:36, and mutant-type: SEQ ID NO:37) which have a base sequence complementary to the base sequence indicated in SEQ ID NO:1 or 2 were used. The sequences of the template oligonucleotides are shown in Table 28. As samples, a sample containing the wild-type template oligonucleotide, a sample containing the mutant-type template oligonucleotide and a sample containing the 1:1 mixture of the wild-type and mutant-type template oligonucleotides were used.

TABLE 27

| name | sequence(5'→3') | Tm (WT: C) | Tm (mt: A) | ∆ | SEQ. ID No. |
|---|---|---|---|---|---|
| 3T-ALKL1196M-WTF12 | cctgCtggagctcatggc-(TAMRA) | 56.9 | 46.6 | 10.3 | 10 |

TABLE 28

| name | sequence(5'→3') | SEQ. ID No. |
|---|---|---|
| ALK WT3souhosa1306 | cgccatgagctccaGcagga | 36 |
| ALK mt3souhosa1306 | cgccatgagctccaTcagga | 37 |

Tm analysis was carried out in the same manner as in Example 1, except that the respective probes and template nucleic acids of Examples 4 and 5 and the reaction reagents shown below were used and that the changes in the fluorescence intensity originating from the respective fluorescently labeled probes were measured with an excitation wavelength of from 520 nm to 555 nm and a detection wavelength of from 585 nm to 700 nm. The Gene Taq Universal buffer shown in Table 29 was a buffer manufactured by Nippon Gene Co., Ltd.

TABLE 29

| Reaction solution | 1test |
|---|---|
| H$_2$O | 39 |
| 1 × Gene Taq Universal buffer | 5 |
| 10 μM probe | 2 |
| 5 μM complementary strand | 4 |
| | 50 |

(μL)

Figure 12:
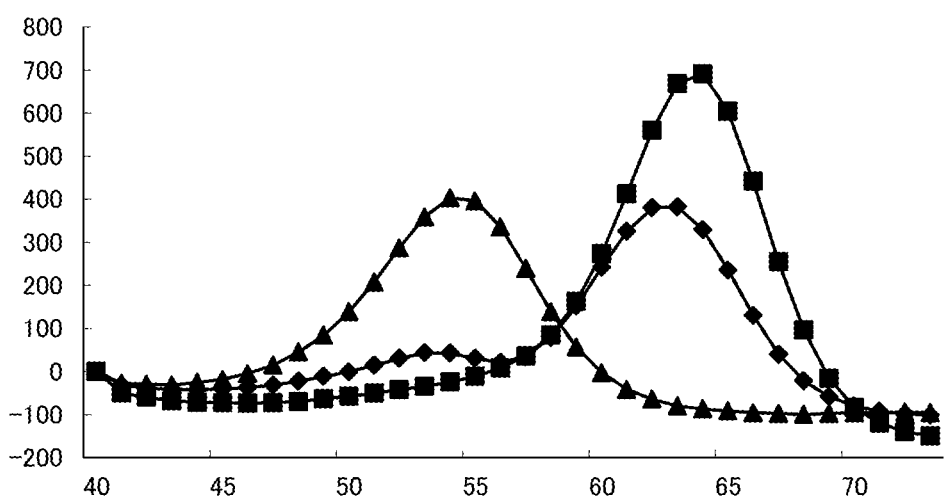
FIG. 12 is a graph showing the result of Tm analysis according to Example 4 of the present invention.
Figure 13:
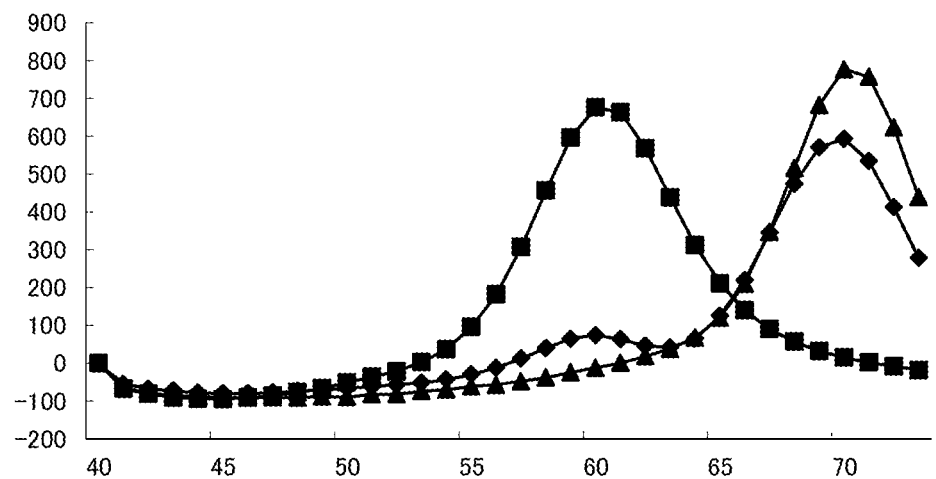
FIG. 13 is a graph showing the result of Tm analysis according to Example 5 of the present invention.

Based on the Tm analysis, FIG. 12 (Example 4) and FIG. 13 (Example 5) showing the changes in the fluorescence value of the probes, respectively, were obtained. In FIGS. 12 and 13, the ordinate indicates the change in the fluorescence intensity per unit time (increase in the d-fluorescence intensity/t), and the abscissa indicates the temperature (° C.). In FIGS. 12 and 13, the pattern indicated with lozenges represents the results obtained by using the wild-type template oligonucleotide as the template nucleotide; the pattern indicated with squares represents the results obtained by using the mutant-type template oligonucleotide as the template nucleic acid; and the pattern indicated with triangles represents the results obtained by using the 1:1 mixture of the wild-type and mutant-type template oligonucleotides as the template nucleic acid.

In Example 4, as shown in FIG. 12, a peak was observed at 54° C. for the wild-type sample and a peak was observed at 64° C. for the ALK(L1196M) mutant-type sample. Two distinguishable peaks were also observed at 53° C. and 63° C. for the sample containing 1:1 mixture of the wild-type and mutant-type nucleic acids. Thus, it was able to favorably detect the presence or absence of the ALK(L1196M) mutation.

In Example 5, as shown in FIG. 13, a peak was observed at 70° C. for the wild-type sample and a peak was observed at 60° C. for the ALK(L1196M) mutant-type sample. Two distinguishable peaks were also observed at 60° C. and 70° C. for the sample containing 1:1 mixture of the wild-type and mutant-type nucleic acids. Thus, it was able to favorably detect the presence or absence of the ALK(L1196M) mutation.

Comparative Examples 5 and 6

As a probe for detecting the ALK(L1196M) mutation in Comparative Example 5, based on the mutant-type base sequence (SEQ ID NO:1), a probe 3T-ALK-L1196M-mtF9 (SEQ ID NO:38), which is a fluorescently labeled oligonucleotide that is composed of the bases corresponding to the 124th to the 139th bases of the base sequence indicated in SEQ ID NO:1 and has a fluorescently labeled cytosine corresponding to the 139th base, was designed and prepared in accordance with a conventional method (see Table 30). Labeling of the cytosine was performed in accordance with a conventional method.

As template nucleic acids, template oligonucleotides (wild-type: SEQ ID NO:39, and mutant-type: SEQ ID NO:40) which have a base sequence complementary to the base sequence indicated in SEQ ID NO:1 or 2 were used. The sequences of the template oligonucleotides are shown in Table 31. As samples, a sample containing the wild-type template oligonucleotide, a sample containing the mutant-type template oligonucleotide and a sample containing a 1:1 mixture of the wild-type and mutant-type template oligonucleotides were used.

It is noted that, in Table 31, "S" and "R" are bases corresponding to a mutation site other than the ALK(L1196M) mutation, and "S" represents "g or c" and "R" represents "g or a".

TABLE 30

| name | sequence(5'→3') | Tm (WT: C) | Tm (mt: A) | ⊿ | SEQ. ID No. |
|---|---|---|---|---|---|
| 3T-ALKL1196M-mtF9 | ttcatcctgAtggagc-(TAMRA) | 41 | 46 | 4.6 | 38 |

TABLE 31

| name | sequence(5'→3') | SEQ. ID No. |
|---|---|---|
| ALK-L1196M WT | RccccccSgccatRagctccaGcaggatgaacSggggcaggg | 39 |
| ALK-L1196M mt | RccccccSgccatRagctccaTcaggatgaacSggggcaggg | 40 | type template oligonucleotide and a sample containing the 1:1 mixture of the wild-type and mutant-type template oligonucleotides were used.

Tm analysis was carried out in the same manner as in Example 4, except that the respective probes and template nucleic acids of Comparative Examples 5 and 6 were used and that the changes in the fluorescence intensity originating from the respective fluorescently labeled probes were measured with an excitation wavelength of from 520 nm to 555 nm and a detection wavelength of from 585 nm to 700 nm.

TABLE 32

| name | sequence(5'→3') | Tm (WT: C) | Tm (mt: A) | ⊿ | SEQ. ID No. |
|---|---|---|---|---|---|
| 5T-ALKL1196M-WTF11 | (TAMRA)-cccggttcatcctgCtgg-P | 56.5 | 46.1 | 10.4 | 41 |

TABLE 33

| name | sequence(5'→3') | SEQ. ID No. |
|---|---|---|
| ALK WT1souhosa1306 | gctccaGcaggatgaaccggggc | 42 |
| ALK mt1souhosa1306 | gctccaTcaggatgaaccggggc | 43 |

Further, as a probe for detecting the ALK(L1196M) mutation in Comparative Example 6, based on the wild-type base sequence (SEQ ID NO:2), a probe 5T-ALK-L1196M-WTF11 (SEQ ID NO:41), which is a fluorescently labeled oligonucleotide that is composed of the bases corresponding to the 119th to the 136th bases of the base sequence indicated in SEQ ID NO:2 and has a fluorescently labeled cytosine corresponding to the 119th base, was designed and prepared in accordance with a conventional method (see Table 32). Labeling of the cytosine was performed in accordance with a conventional method.

Figure 14:
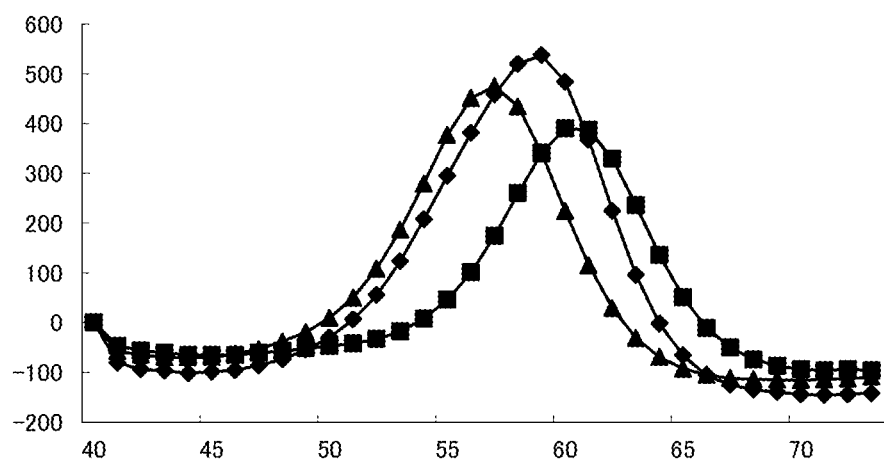
FIG. 14 is a graph showing the result of Tm analysis according to Comparative Example 5 in the present invention.
Figure 15:
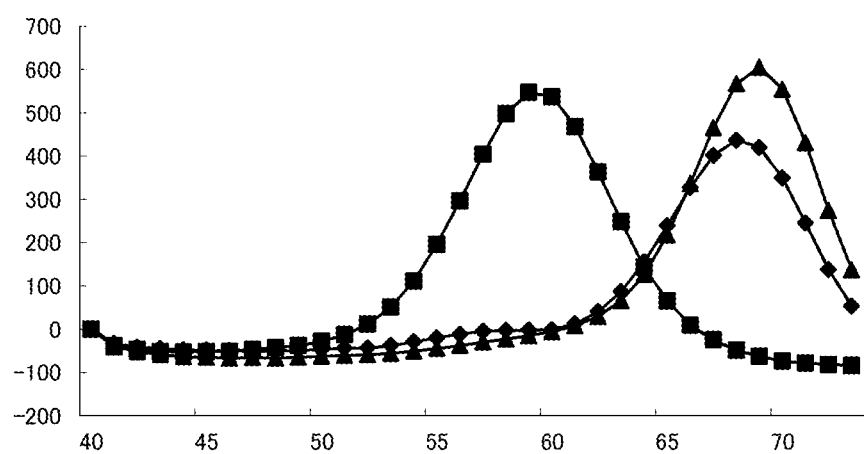
FIG. 15 is a graph showing the result of Tm analysis according to Comparative Example 6 in the present invention.

As template nucleic acids, template oligonucleotides (wild-type: SEQ ID NO:42, and mutant-type: SEQ ID NO:43) which have a base sequence complementary to the base sequence indicated in SEQ ID NO:1 or 2 were used. The sequences of the template oligonucleotides are shown in Table 33. As samples, a sample containing the wild-type template oligonucleotide, a sample containing the mutant- Based on the Tm analysis, FIG. 14 (Comparative Example 5) and FIG. 15 (Comparative Example 6) showing the changes in the fluorescence value of the respective probes were obtained. In FIGS. 14 and 15, the ordinate indicates the change in the fluorescence intensity per unit time (increase in the d-fluorescence intensity/t), and the abscissa indicates the temperature (° C.). In FIGS. 14 and 15, the pattern indicated with lozenges represents the results obtained by using the wild-type template oligonucleotide as the template nucleic acid; the pattern indicated with squares represents the results obtained by using the mutant-type template oligonucleotide as the template nucleic acid; and the pattern indicated with triangles represents the results obtained by using the 1:1 mixture of the wild-type and mutant-type template oligonucleotides as the template nucleic acid.

In Comparative Example 5, as shown in FIG. 14, a peak was observed at 57° C. for the wild-type sample and a peak was observed at 60° C. for the mutant-type sample. Meanwhile, only one peak was observed at 59° C. for the sample containing the mixture of the wild-type and mutant-type nucleic acids.

Furthermore, in Comparative Example 6, as shown in FIG. 15, a peak was observed at 69° C. for the wild-type sample and a peak was observed at 59° C. for the mutant-type sample. Meanwhile, only one distinct peak was observed at 59° C. for the sample containing the mixture of the wild-type and mutant-type nucleic acids.

Accordingly, it was found that neither of the probes of Comparative Examples 5 and 6 are suitable for detecting the ALK(L1196M) mutation.

Therefore, according to the present invention, mutations in the ALK gene, namely the ALK(L1196M) and ALK (C1156Y) mutations, can be easily detected with good sensitivity at the same time or separately.

By this, the efficacy of a drug based on an ALK gene mutation, such an anticancer agent containing an ALK inhibitor as an active ingredient, can be easily evaluated.

The disclosure of Japanese Patent Application No. 2012-210057, which was filed on Sep. 24, 2012, and Japanese Patent Application No. 2013-186532, which was filed on Sep. 9, 2013, are hereby incorporated by reference in its entirety.

All references, patent applications, and technical standards described in the present specification are herein incorporated in their entirety by reference into the specification, to the same extent as if each individual reference, patent application or technical standard was specifically and individually indicated to be incorporated herein by reference.

What is claimed is:

1. A mutation detection probe comprising a fluorescent dye and an oligonucleotide,
   wherein the oligonucleotide consists of an oligonucleotide selected from the group consisting of SEQ ID NO: 5, 6, 7, 9 and 10, and
   the nucleotide bases at the first position from the 3' end of SEQ ID NO: 5, 6 and 10, and at the first position from the 5' end of SEQ ID NO: 7 and 9 are labeled with the fluorescent dye.

2. The mutation detection probe according to claim 1, wherein the fluorescently labeled oligonucleotide emits fluorescence when not hybridized to a target sequence, and the fluorescence intensity of the fluorescently labeled oligonucleotide when hybridized to the target sequence is decreased as compared to when not hybridized to the target sequence.

3. The mutation detection probe according to claim 1, which is a probe for melting curve analysis.

4. A method of detecting a mutation in the ALK gene, the method comprising:
   (I) bringing a mutation detection probe according to claim 1 into contact with a single stranded nucleic acid contained in a sample to hybridize the probe to the single-stranded nucleic acid, to obtain a hybrid;
   (II) dissociating the hybrid by changing a temperature of the sample containing the hybrid and measuring a change in a fluorescence signal caused by dissociation of the hybrid;
   (III) determining a Tm value, which is a dissociation temperature of the hybrid, based on the change in the fluorescence signal; and
   (IV) detecting the presence of a mutation in the ALK gene in the single-stranded nucleic acid contained in the sample, based on the Tm value.

5. The method according to claim 4, further comprising:
   amplifying the nucleic acid prior to or simultaneously with the process (I) of obtaining a hybrid.

6. A method of detecting a mutation in the ALK gene, the method comprising:
   (I) bringing a mutation detection probe according to claim 1 into contact with a single stranded nucleic acid contained in a sample to hybridize the probe to the single-stranded nucleic acid, to obtain a hybrid;
   (II) dissociating the hybrid by changing a temperature of the sample containing the hybrid and measuring a change in a fluorescence signal caused by dissociation of the hybrid;
   (III) determining a Tm value, which is a dissociation temperature of the hybrid, based on the change in the fluorescence signal; and
   (IV) detecting the presence of a mutation in the ALK gene in the single-stranded nucleic acid contained in the sample, based on the Tm value; further comprising:
   amplifying the nucleic acid using primers
comprising SEQ ID NO:14 and 15.

7. A method of determining tolerance to a drug or evaluating efficacy of a drug, the method comprising:
   detecting a mutation in the ALK gene by the method of detecting a mutation according to claim 4; and
   determining tolerance to a drug or efficacy of the drug based on the detecting.

8. A reagent kit for detecting a mutation in the ALK gene, the reagent kit comprising the mutation detection probe according to claim 1.

9. The reagent kit according to claim 8, further comprising at least one
   primer for amplifying a base sequence containing a region to which SEQ ID NO: 5, 6, 7, 9 or 10 hybridizes.

10. The mutation detection probe according to claim 1, wherein the mutation detection probe consists of the fluorescent dye and the oligonucleotide.

11. The reagent kit according to claim 8, further comprising a second probe comprising a fluorescent dye and an oligonucleotide consisting of SEQ ID NO: 8, wherein the nucleotide base at the first position from the 3' end of SEQ ID NO: 8 is labeled with the fluorescent dye.

* * * * *

SEQUENCE LISTING

```
<160> NUMBER OF SEQ ID NOS: 43

<210> SEQ ID NO 1
<211> LENGTH: 300
<212> TYPE: DNA
<213> ORGANISM: Homo sapiens

<400> SEQUENCE: 1
agtttaagat ttgcccagac tcagctcagt taattttggt tacatccctc tctgctctgc      60
agcaaattca accaccagaa cattgttcgc tgcattgggg tgagcctgca atccctgccc     120
cggttcatcc tgatggagct catggcgggg ggagacctca agtccttcct ccgagagacc     180
cgccctcgcc cggtgagtga gaaccagtct ttgctgcagt tgttgtgcca aggacaggag     240
caaggatgga aggagcaaga gtgggcagcc tgggtagcaa gttcctcgat ggaacccagg     300

<210> SEQ ID NO 2
<211> LENGTH: 300
<212> TYPE: DNA
<213> ORGANISM: Homo sapiens

<400> SEQUENCE: 2
agtttaagat ttgcccagac tcagctcagt taattttggt tacatccctc tctgctctgc      60
agcaaattca accaccagaa cattgttcgc tgcattgggg tgagcctgca atccctgccc     120
cggttcatcc tgctggagct catggcgggg ggagacctca agtccttcct ccgagagacc     180
cgccctcgcc cggtgagtga gaaccagtct ttgctgcagt tgttgtgcca aggacaggag     240
caaggatgga aggagcaaga gtgggcagcc tgggtagcaa gttcctcgat ggaacccagg     300

<210> SEQ ID NO 3
<211> LENGTH: 300
<212> TYPE: DNA
<213> ORGANISM: Homo sapiens

<400> SEQUENCE: 3
gtctcctctt gtcttctcct ttgcacaggg gtctgggcca tggcgccttt ggggaggtgt      60
atgaaggcca ggtgtccgga atgcccaacg acccaagccc cctgcaagtg gctgtgaagg     120
taagaagtgg ctcactcttg agcctgccct tggcttgcgg actctgtagg ctgcagttct     180
cagctcacag cctcctcctc ctccccaccc tccccttctc tgcccagacg ctgcctgaag     240
tgtactctga acaggacgaa ctggatttcc tcatggaagc cctgatcatc aggtaaagcc     300

<210> SEQ ID NO 4
<211> LENGTH: 300
<212> TYPE: DNA
```

<213> ORGANISM: Homo sapiens

<400> SEQUENCE: 4

```
gtctcctctt gtcttctcct ttgcacaggg gtctgggcca tggcgccttt ggggaggtgt    60
atgaaggcca ggtgtccgga atgcccaacg acccaagccc cctgcaagtg gctgtgaagg   120
taagaagtgg ctcactcttg agcctgccct tggcttgcgg actctgtagg ctgcagttct   180
cagctcacag cctcctcctc ctccccaccc tcccctttctc tgcccagacg ctgcctgaag   240
tgtgctctga acaggacgaa ctggatttcc tcatggaagc cctgatcatc aggtaaagcc   300
```

<210> SEQ ID NO 5
<211> LENGTH: 17
<212> TYPE: DNA
<213> ORGANISM: Artificial Sequence
<220> FEATURE:
<223> OTHER INFORMATION: 3PB-ALKL1196M-mt-R1

<400> SEQUENCE: 5

```
gctccatcag gatgaac                                                    17
```

<210> SEQ ID NO 6
<211> LENGTH: 19
<212> TYPE: DNA
<213> ORGANISM: Artificial Sequence
<220> FEATURE:
<223> OTHER INFORMATION: 3T-ALKL1196M-mt-F7

<400> SEQUENCE: 6

```
gttcatcctg atggagctc                                                  19
```

<210> SEQ ID NO 7
<211> LENGTH: 16
<212> TYPE: DNA
<213> ORGANISM: Artificial Sequence
<220> FEATURE:
<223> OTHER INFORMATION: 5T-ALK-L1196M-R1

<400> SEQUENCE: 7

```
ctccagcagg atgaac                                                     16
```

<210> SEQ ID NO 8
<211> LENGTH: 18
<212> TYPE: DNA
<213> ORGANISM: Artificial Sequence
<220> FEATURE:
<223> OTHER INFORMATION: 3T-ALKC1156Y-mt-F2

<400> SEQUENCE: 8

```
ctgaagtgta ctctgaac                                                   18
```

<210> SEQ ID NO 9
<211> LENGTH: 17
<212> TYPE: DNA
<213> ORGANISM: Artificial Sequence
<220> FEATURE:
<223> OTHER INFORMATION: 5T-ALKL1196M-mt-R5

<400> SEQUENCE: 9

```
ccatgagctc catcagg                                                    17
```

<210> SEQ ID NO 10
<211> LENGTH: 18
<212> TYPE: DNA
<213> ORGANISM: Artificial Sequence

```
<220> FEATURE:
<223> OTHER INFORMATION: 3T-ALK-L1196M-WTF12

<400> SEQUENCE: 10
cctgctggag ctcatggc                                                   18

<210> SEQ ID NO 11
<211> LENGTH: 23
<212> TYPE: DNA
<213> ORGANISM: Artificial Sequence
<220> FEATURE:
<223> OTHER INFORMATION: ALK C1156Y-F1

<400> SEQUENCE: 11
ggactctgta ggctgcagtt ctc                                             23

<210> SEQ ID NO 12
<211> LENGTH: 28
<212> TYPE: DNA
<213> ORGANISM: Artificial Sequence
<220> FEATURE:
<223> OTHER INFORMATION: ALK C1156Y-R4

<400> SEQUENCE: 12
tgatcagggc ttccatgagg aaatccag                                        28

<210> SEQ ID NO 13
<211> LENGTH: 21
<212> TYPE: DNA
<213> ORGANISM: Artificial Sequence
<220> FEATURE:
<223> OTHER INFORMATION: ALK L1196M F-1

<400> SEQUENCE: 13
cattggggtg agcctgcaat c                                               21

<210> SEQ ID NO 14
<211> LENGTH: 28
<212> TYPE: DNA
<213> ORGANISM: Artificial Sequence
<220> FEATURE:
<223> OTHER INFORMATION: ALK L1196M-mt-F10

<400> SEQUENCE: 14
tgcatcaccc tgccccggtt catcctga                                        28

<210> SEQ ID NO 15
<211> LENGTH: 26
<212> TYPE: DNA
<213> ORGANISM: Artificial Sequence
<220> FEATURE:
<223> OTHER INFORMATION: ALK L1196M-WT-F6

<400> SEQUENCE: 15
ctacgacctg ccccggttca acctgc                                          26

<210> SEQ ID NO 16
<211> LENGTH: 26
<212> TYPE: DNA
<213> ORGANISM: Artificial Sequence
<220> FEATURE:
<223> OTHER INFORMATION: ALK L1196M R-2

<400> SEQUENCE: 16
cttggcacaa caactgcagc aaagac                                          26
```

<210> SEQ ID NO 17
<211> LENGTH: 38
<212> TYPE: DNA
<213> ORGANISM: Artificial Sequence
<220> FEATURE:
<223> OTHER INFORMATION: ALK L1196M R-3

<400> SEQUENCE: 17
ggacggacgg accttggcac aacaactgca gcaaagac         38

<210> SEQ ID NO 18
<211> LENGTH: 300
<212> TYPE: DNA
<213> ORGANISM: Artificial Sequence
<220> FEATURE:
<223> OTHER INFORMATION: Mt ALK (L1196M ) insert

<400> SEQUENCE: 18
agtttaagat tgcccagac tcagctcagt taattttggt tacatccctc tctgctctgc      60
agcaaattca accaccagaa cattgttcgc tgcattgggg tgagcctgca atccctgccc     120
cggttcatcc tgatggagct catggcgggg ggagacctca agtccttcct ccgagagacc     180
cgccctcgcc cggtgagtga gaaccagtct ttgctgcagt tgttgtgcca aggacaggag     240
caaggatgga aggagcaaga gtgggcagcc tgggtagcaa gttcctcgat ggaacccagg     300

<210> SEQ ID NO 19
<211> LENGTH: 300
<212> TYPE: DNA
<213> ORGANISM: Artificial Sequence
<220> FEATURE:
<223> OTHER INFORMATION: Wt ALK (L1196M ) insert

<400> SEQUENCE: 19
agtttaagat tgcccagac tcagctcagt taattttggt tacatccctc tctgctctgc      60
agcaaattca accaccagaa cattgttcgc tgcattgggg tgagcctgca atccctgccc     120
cggttcatcc tgctggagct catggcgggg ggagacctca agtccttcct ccgagagacc     180
cgccctcgcc cggtgagtga gaaccagtct ttgctgcagt tgttgtgcca aggacaggag     240
caaggatgga aggagcaaga gtgggcagcc tgggtagcaa gttcctcgat ggaacccagg     300

<210> SEQ ID NO 20
<211> LENGTH: 300
<212> TYPE: DNA
<213> ORGANISM: Artificial Sequence
<220> FEATURE:
<223> OTHER INFORMATION: Mt ALK (C1156Y ) insert

<400> SEQUENCE: 20
gtccggaatg cccaacgacc caagccaagc cccctgcaag tggctgtgaa ggtaagaagt      60
ggctcactct tgagcctgcc cttggcttgc ggactctgta ggctgcagtt ctcagctcac     120
agcctcctcc tcctccccac cctcccctc tctgcccaga cgctgcctga agtgtactct      180
gaacaggacg aactggattt cctcatggaa gccctgatca tcaggtaaag ccacagagag     240
acaccctcac cccaactccc ctctgccccc aaagaacctg gagaggtttc taacagatcg     300

<210> SEQ ID NO 21
<211> LENGTH: 300
<212> TYPE: DNA
<213> ORGANISM: Artificial Sequence
<220> FEATURE:
<223> OTHER INFORMATION: Wt ALK (C1156Y ) insert -continued

<400> SEQUENCE: 21

```
gtccggaatg cccaacgacc caagccaagc ccctgcaag tggctgtgaa ggtaagaagt    60
ggctcactct tgagcctgcc cttggcttgc ggactctgta ggctgcagtt ctcagctcac   120
agcctcctcc tcctcccac cctccccttc tctgcccaga cgctgcctga agtgtgctct   180
gaacaggacg aactggattt cctcatggaa gccctgatca tcaggtaaag ccacagagag   240
acaccctcac cccaactccc ctctgccccc aaagaacctg agaggtttc taacagatcg   300
```

<210> SEQ ID NO 22
<211> LENGTH: 13
<212> TYPE: DNA
<213> ORGANISM: Artificial Sequence
<220> FEATURE:
<223> OTHER INFORMATION: 3PB-ALKL1196M-mt-F1

<400> SEQUENCE: 22

```
cctgatggag ctc                                                       13
```

<210> SEQ ID NO 23
<211> LENGTH: 27
<212> TYPE: DNA
<213> ORGANISM: Artificial Sequence
<220> FEATURE:
<223> OTHER INFORMATION: Comp. oligo L1196M (WT)

<400> SEQUENCE: 23

```
atgagctcca gcaggatgaa ccggggc                                        27
```

<210> SEQ ID NO 24
<211> LENGTH: 27
<212> TYPE: DNA
<213> ORGANISM: Artificial Sequence
<220> FEATURE:
<223> OTHER INFORMATION: Comp. oligo L1196M (Mt)

<400> SEQUENCE: 24

```
atgagctcca tcaggatgaa ccggggc                                        27
```

<210> SEQ ID NO 25
<211> LENGTH: 17
<212> TYPE: DNA
<213> ORGANISM: Artificial Sequence
<220> FEATURE:
<223> OTHER INFORMATION: 5T-ALK-L1196M-mt-F5

<400> SEQUENCE: 25

```
catcctgatg gagctca                                                   17
```

<210> SEQ ID NO 26
<211> LENGTH: 17
<212> TYPE: DNA
<213> ORGANISM: Artificial Sequence
<220> FEATURE:
<223> OTHER INFORMATION: 3T-C1156Y-mt-F4

<400> SEQUENCE: 26

```
cgctgcctga agtgtac                                                   17
```

<210> SEQ ID NO 27
<211> LENGTH: 27
<212> TYPE: DNA
<213> ORGANISM: Artificial Sequence
<220> FEATURE:

```
<223> OTHER INFORMATION: Comp. oligo C1156Y (WT)

<400> SEQUENCE: 27
gttcagagca cacttcaggc agcgtct                                27

<210> SEQ ID NO 28
<211> LENGTH: 27
<212> TYPE: DNA
<213> ORGANISM: Artificial Sequence
<220> FEATURE:
<223> OTHER INFORMATION: Comp. oligo C1156Y (Mt)

<400> SEQUENCE: 28
gttcagagta cacttcaggc agcgtct                                27

<210> SEQ ID NO 29
<211> LENGTH: 25
<212> TYPE: DNA
<213> ORGANISM: Artificial Sequence
<220> FEATURE:
<223> OTHER INFORMATION: ALK-WT-F
<220> FEATURE:
<221> NAME/KEY: misc_feature
<222> LOCATION: (3)..(3)
<223> OTHER INFORMATION: g or c
<220> FEATURE:
<221> NAME/KEY: misc_feature
<222> LOCATION: (22)..(22)
<223> OTHER INFORMATION: t or c

<400> SEQUENCE: 29
ccsgttcatc ctgctggagc tyatg                                  25

<210> SEQ ID NO 30
<211> LENGTH: 25
<212> TYPE: DNA
<213> ORGANISM: Artificial Sequence
<220> FEATURE:
<223> OTHER INFORMATION: ALK-mt-F
<220> FEATURE:
<221> NAME/KEY: misc_feature
<222> LOCATION: (3)..(3)
<223> OTHER INFORMATION: g or c
<220> FEATURE:
<221> NAME/KEY: misc_feature
<222> LOCATION: (22)..(22)
<223> OTHER INFORMATION: t or c

<400> SEQUENCE: 30
ccsgttcatc ctgatggagc tyatg                                  25

<210> SEQ ID NO 31
<211> LENGTH: 17
<212> TYPE: DNA
<213> ORGANISM: Artificial Sequence
<220> FEATURE:
<223> OTHER INFORMATION: 3T-ALK-L1196M-F5

<400> SEQUENCE: 31
gttcatcctg ctggagc                                           17

<210> SEQ ID NO 32
<211> LENGTH: 27
<212> TYPE: DNA
<213> ORGANISM: Artificial Sequence
<220> FEATURE:
<223> OTHER INFORMATION: ALKL1196MWTR

<400> SEQUENCE: 32
```

```
atgagctcca gcaggatgaa ccggggc                                              27

<210> SEQ ID NO 33
<211> LENGTH: 27
<212> TYPE: DNA
<213> ORGANISM: Artificial Sequence
<220> FEATURE:
<223> OTHER INFORMATION: ALKL1196MmtR

<400> SEQUENCE: 33
atgagctcca tcaggatgaa ccggggc                                              27

<210> SEQ ID NO 34
<211> LENGTH: 19
<212> TYPE: DNA
<213> ORGANISM: Artificial Sequence
<220> FEATURE:
<223> OTHER INFORMATION: ALK WT2souhosa1306

<400> SEQUENCE: 34
tcctgctgga gctcatggc                                                       19

<210> SEQ ID NO 35
<211> LENGTH: 19
<212> TYPE: DNA
<213> ORGANISM: Artificial Sequence
<220> FEATURE:
<223> OTHER INFORMATION: ALK mt2souhosa1306

<400> SEQUENCE: 35
tcctgatgga gctcatggc                                                       19

<210> SEQ ID NO 36
<211> LENGTH: 20
<212> TYPE: DNA
<213> ORGANISM: Artificial Sequence
<220> FEATURE:
<223> OTHER INFORMATION: ALK WT3souhosa1306

<400> SEQUENCE: 36
cgccatgagc tccagcagga                                                      20

<210> SEQ ID NO 37
<211> LENGTH: 20
<212> TYPE: DNA
<213> ORGANISM: Artificial Sequence
<220> FEATURE:
<223> OTHER INFORMATION: ALK mt3souhosa1306

<400> SEQUENCE: 37
cgccatgagc tccatcagga                                                      20

<210> SEQ ID NO 38
<211> LENGTH: 16
<212> TYPE: DNA
<213> ORGANISM: Artificial Sequence
<220> FEATURE:
<223> OTHER INFORMATION: 3T-ALKL1196M-mtF9

<400> SEQUENCE: 38
ttcatcctga tggagc                                                          16

<210> SEQ ID NO 39
<211> LENGTH: 40
<212> TYPE: DNA
```

```
<213> ORGANISM: Artificial Sequence
<220> FEATURE:
<223> OTHER INFORMATION: ALK-L1196M WT-R

<400> SEQUENCE: 39 ccccsgcca tragctccag caggatgaac sggggcaggg                          40

<210> SEQ ID NO 40
<211> LENGTH: 40
<212> TYPE: DNA
<213> ORGANISM: Artificial Sequence
<220> FEATURE:
<223> OTHER INFORMATION: ALK-L1196M mt-R

<400> SEQUENCE: 40 ccccsgcca tragctccat caggatgaac sggggcaggg                          40

<210> SEQ ID NO 41
<211> LENGTH: 18
<212> TYPE: DNA
<213> ORGANISM: Artificial Sequence
<220> FEATURE:
<223> OTHER INFORMATION: 5T-ALK-L1196M-WTF11

<400> SEQUENCE: 41
cccggttcat cctgctgg                                                 18

<210> SEQ ID NO 42
<211> LENGTH: 23
<212> TYPE: DNA
<213> ORGANISM: Artificial Sequence
<220> FEATURE:
<223> OTHER INFORMATION: ALK WT1souhosa1306

<400> SEQUENCE: 42
gctccagcag gatgaaccgg ggc                                           23

<210> SEQ ID NO 43
<211> LENGTH: 23
<212> TYPE: DNA
<213> ORGANISM: Artificial Sequence
<220> FEATURE:
<223> OTHER INFORMATION: ALK mt1souhosa1306

<400> SEQUENCE: 43
gctccatcag gatgaaccgg ggc                                           23
```